(12) United States Patent
Soares

(10) Patent No.: US 9,193,776 B2
(45) Date of Patent: Nov. 24, 2015

(54) PEPTIDE ANTAGONISTS OF THE CALCITONIN CGRP FAMILY OF PEPTIDE HORMONES AND THEIR USE

(71) Applicant: Christopher J. Soares, La Jolla, CA (US)

(72) Inventor: Christopher J. Soares, La Jolla, CA (US)

(*) Notice: Subject to any disclaimer, the term of this patent is extended or adjusted under 35 U.S.C. 154(b) by 0 days.

(21) Appl. No.: 13/821,936

(22) PCT Filed: Jan. 25, 2013

(86) PCT No.: PCT/US2013/023260
§ 371 (c)(1),
(2) Date: Mar. 8, 2013

(87) PCT Pub. No.: WO2013/112912
PCT Pub. Date: Aug. 1, 2013

(65) Prior Publication Data
US 2014/0329752 A1    Nov. 6, 2014

Related U.S. Application Data

(60) Provisional application No. 61/591,236, filed on Jan. 26, 2012.

(51) Int. Cl.
| | |
|---|---|
| *A61K 38/23* | (2006.01) |
| *A61P 5/22* | (2006.01) |
| *C07K 14/585* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 14/575* | (2006.01) |

(52) U.S. Cl.
CPC ......... *C07K 14/57527* (2013.01); *C07K 14/585* (2013.01); *A61K 38/00* (2013.01)

(58) Field of Classification Search
CPC . A61K 38/00; C07K 14/57527; C07K 14/585
See application file for complete search history.

(56) References Cited

U.S. PATENT DOCUMENTS

| | | | |
|---|---|---|---|
| 3,940,475 A | 2/1976 | Gross | |
| 4,179,337 A | 12/1979 | Davis | |
| 4,301,144 A | 11/1981 | Iwashita | |
| 4,496,689 A | 1/1985 | Mitra | |
| 4,522,752 A | 6/1985 | Sisto | |
| 4,530,838 A | 7/1985 | Evans | |
| 4,640,835 A | 2/1987 | Shimizu | |
| 4,670,417 A | 6/1987 | Iwasaki | |
| 4,791,192 A | 12/1988 | Nakagawa | |
| 5,364,934 A | 11/1994 | Drayna | |
| 5,698,401 A | 12/1997 | Fesik | |
| 5,733,569 A | 3/1998 | Azria | |
| 5,804,390 A | 9/1998 | Fesik | |
| 7,812,120 B2 | 10/2010 | Quay | |
| 8,114,958 B2 * | 2/2012 | Soares et al. | 530/307 |
| 8,263,545 B2 * | 9/2012 | Levy et al. | 514/1.1 |
| 2008/0312157 A1 * | 12/2008 | Levy et al. | 514/15 |
| 2009/0264368 A1 | 10/2009 | Goldberg | |
| 2010/0016229 A1 | 1/2010 | Sarubbi | |

FOREIGN PATENT DOCUMENTS

| | | | |
|---|---|---|---|
| EP | 045665 | 10/1982 | |
| EP | 0253464 | 5/1992 | |
| EP | 613683 | 9/1994 | |
| WO | WO 93/25221 | 12/1993 | |
| WO | WO 94/17784 | 8/1994 | |
| WO | WO 95/34326 | 12/1995 | |
| WO | WO2006086769 | * 8/2006 | C07K 14/575 |
| WO | WO 2006/105527 A2 | 10/2006 | |

OTHER PUBLICATIONS

Geneseq Database [Online] Feb. 7, 2003, "Human calcitonin gene-related peptide 1." XP002694858, retrieved from EBI accession No. GSP:ABP55105, Database accession No. ABP55105.
Taylor, C.K. et al. (2006) "Pharmacological characterization of novel alpha-Calcitonin Gene-Related Peptide (CGRP) receptor peptide antagonists that are selective for human CGRP receptors" *J. Pharmacol. Exp. Ther.* 319 (2): 749-757.
PCT International Preliminary Report on Patentability, Aug. 7, 2014, pp. 1-10.
Almquist, et al. (1980) "Synthesis and biological activity of a ketomethylene analogue of a tripeptide inhibitor of angiotensin converting enzyme" *J. Med. Chem.* 23:1392-1398.
Altschul et al. (1996) "Local alignment statistics" *Methods in Enzymology*, 266:460-480.
Altschul et al. (1997) "Gapped BLAST and PSI-BLAST: a new generation of protein database search programs." *Nucleic Acids Res.*, 25:3389-3402.
Andreu, et al. (1994) "Formation of disulfide bonds in synthetic peptides and proteins" *Meth. Mol. Bio.* 35(7):91-169.
Ashina, et al. (2000) "Evidence for increased plasma levels of calcitonin gene-related peptide in migraine outside of attacks" *Pain* 86(1-2)133-8.
Barker, et al. (1992) "Cyclic RGD peptide analogues as antiplatelet antithrombotics" *J. Med. Chem.* 35:2040-2048.
Christopoulos, et al. (1999) "Multiple amylin receptors arise from receptor activity-modifying protein interaction with the calcitonin receptor gene product." *Mol. Pharmacol.* 56:235-242.

(Continued)

*Primary Examiner* — Marcela M Cordero Garcia
(74) *Attorney, Agent, or Firm* — Knobbe, Martens, Olson & Bear LLP

(57) ABSTRACT

The embodiments provide a modified calcitonin gene-related peptide antagonist including an N-terminal fragment of modified calcitonin gene-related peptide or related protein family member where at least two residues of the N-terminal fragment are cysteine (Cys) and at least one amino acid comprises a non-threonine substitution of a threonine (Thr) residue; a central core where the central core comprises an α-helix; and a C-terminal fragment of modified calcitonin gene-related peptide or related protein family member comprising a C-terminal amide and where at least one amino acid of the C-terminal fragment is phenylalanine (Phe), proline (Pro), tyrosine (Tyr) or hydroxyproline (Hyp) or pharmaceutically acceptable salt thereof, as well as compositions, including pharmaceutical compositions, comprising a subject peptide. The embodiments further provide treatment methods, including methods of treating a migraine, the methods generally involving administering to an individual in need thereof an effective amount of a subject peptide or composition.

28 Claims, No Drawings

(56) References Cited

OTHER PUBLICATIONS

Durham and Vause (2010) "Calcitonin gene-related peptide (CGRP) receptor antagonists in the treatment of migraine." *CNS Drugs* 24(7):539-548.
Edvinsson L. (2001) "Calcitonin gene-related peptide (CGRP) and the pathophysiology of headache: therapeutic implications." *CNS Drugs* 15(10):745-53.
Farmer, P.S. (1980) *Drug Design* E.J. Ariens, ed. Academic Press, New York, 10:119-143.
Fauchere, J. (1986) "Elements for the rational design of peptide drugs" *Adv. Drug Res.* 15:29-69.
Fingl et al. 1975, in "The Pharmacological Basis of Therapeutics", Ch.1, p. 1-46.
Freidinger, R.M. (1989) "Non-peptide ligands for peptide receptors." *Trends Pharmacol. Sci.* 10:270-274.
Gante, (1994) "Peptidomimetics—Tailored Enzyme Inhibitors" *Angew. Chem. Int. Ed. Engl.* 33:1699-1720.
Goadsby, et al. (1990) "Vasoactive peptide release in the extracerebral circulation of humans during migraine headache." *Ann. Neurol.* 28:183-7.
Goodman et al. (1981) "The Synthesis and Conformational Analysis of Retro-Inverso Analogues of Biologically Active Molecules", *Perspectives in Peptide Chemistry* pp. 283-294.
Grant, A.D. (2002) "Evidence of a role for NK1 and CGRP receptors in mediating neurogenic vasodilatation in the mouse ear" *Brit. J Pharmacol.* 135:356-362.
Hann (1982) "On the double bond isostere of the peptide bond: preparation of an enkephalin analogue" *J. Chem. Soc. Perkin. Trans.* I 307-314.
Hay, et al. (2001) Knockouts and transgenics confirm the importance of adrenomedullin in the vasculature. *Trends Pharmacol. Sci.* 22:57-59.
Holladay, et al. (1983) "Synthesis of Hydroxyethylene and Ketomethylene Dipeptide Isoteres" *Tetrahedron Lett.* 24:4401-4404.
Hruby, et al. (1990) "Emerging approaches in the molecular design of receptor-selective peptide ligands: conformational, topographical and dynamic considerations" *Biochem. J.* 268(2):249-262.
Hudson, et al. (1979) "Conformational restrictions of biologically active peptides via amino acid side chain groups." *Int. J. Pept. Prot. Res.* 14:177-185.
International Search Report mailed Apr. 17, 2013 received in PCT/US2013/023260, filed Jan. 25, 2013.
IUPAC-IUB Joint Commission on Biochemical Nomenclature (JCBN). (1984) Nomenclature and symbolism for amino acids and peptides. Recommendations 1983.*Biochem. J.*, 219, 345-373.
James, G.L. et al. (1993) "Benzodiazepine peptidomimetics: potent inhibitors of Ras farnesylation in animal cells." *Science* 260:1937-1942.
Jennings-White, et al. (1982) "Synthesis of Ketomethylene Analogs of Dipeptides," *Tetrahedron Letter.* 23:2533-2534.
Joshi, A., (1994) "Microparticulates for ophthalmic drug delivery." *J. Ocul. Pharmacol.*, 10(1):29-45.
Lassen, et al. (2002) "CGRP may play a causative role in migraine." *Cephalalgia* 22(1):54-61.
Luthman, et al. 1996 *A Textbook of Drug Design and Development*, 14:386-406, 2nd Ed., Harwood Academic Publishers.
March, 1992 *Advanced Organic Chemistry*, 4th Ed., John Wiley & Sons, New York, p. 393-396.
Mayer et al., (1996) "Efficacy of a novel hydrogel formulation in human volunteers." *Ophthalmologica*, 210(2): 101-3.
McLatchie et al. (1998) "RAMPs regulate the transport and ligand specificity of the calcitonin-receptor-like receptor." *Nature* 393:333-339.
Merck Updates Status of Clinical Development Programs for Investigational CGRP Receptor Antagonist Treatments for Acute Migraine; MK-3207 Clinical Development Discontinued. Sep. 10, 2009. Merck & Co., Inc. Web. Jun. 1, 2011.
Mimeault, M. et al., (1992) "Structure-activity study of hCGRP8-37, a calcitonin gene-related peptide receptor antagonist." *J. Med. Chem.* 35:2163-2168.

Miret, et al. (2002) "Functional expression of heteromeric calcitonin gene-related peptide and adrenomedullin receptors in yeast" *JBC* 277(9):6881-6887.
Monfardini, C, et al. (1995) "A branched monomethoxypoly(ethylene glycol) for protein modification." *Bioconjugate Chem* 6:62-69.
Mordenti (1999) "Intraocular Pharmacokinetics and Safety of a Humanized Monoclonal Antibody in Rabbits after Intravitreal Administration of a Solution or a PLGA Microsphere Formulation," *Toxicol. Sci.*, 52(1):101-6.
Morley, (1980) "K+ channel openers and suppression of airway hyperreactivity." *Trends. Pharm. Sci.* pp. 463-468, (general review).
Moskowitz (1992) "Neurogenic versus vascular mechanisms of sumatriptan and ergot alkaloids in migraine." *Trends Pharmacol. Sci.* 13:307-311.
Mulder, et al. 2000, *Am. J. Physiol.* 278:E684-E691.
Or, et al. (1991) "Cysteine alkylation in unprotected peptides: Synthesis of a carbavasopressin analogue by intramolecular cysteine alkylation" *J. Org. Chem.* 56:3146-3149.
Pellecchia, et al. (2002) "NMR in drug discovery." *Nature Rev Drug Disc* 1:211.
Poyner et al. (2002) "International Union of Pharmacology. XXXII. The Mammalian Calcitonin Gene-Related Peptides, Adrenomedullin, Amylin, and Calcitonin Receptors" *Pharmacol. Rev.* 54:233-246.
Poyner, D. (1992) "Calcitonin gene-related peptide: multiple actions, multiple receptors." *Pharmac. Ther.* 56:23-51.
Rizo, et al. (1992) "Constrained peptides: models of bioactive peptides and protein substructures." *Ann. Rev. Biochem.* 61:387.
Roh et al. (2004) "Intermedin Is a Calcitonin/Calcitonin Gene-related Peptide Family Peptide Acting through the Calcitonin Receptor-like Receptor/Receptor Activity-modifying Protein Receptor Complexes" *JBC* 279(8):7264-7274.
Rovero, P. et al. (1992) "CGRP antagonist activity of short C-terminal fragments of human alpha CGRP, CGRP(23-37) and CGRP(19-37)." *Peptides* 13:1025-1027.
Salmon et al. (1999) Modulation of morphine analgesia in alphaCGRP mutant mice. *Neuroreport* 10:849-854.
Salmon, al. et al. (2001) "Altered neuroadaptation in opiate dependence and neurogenic inflammatory nociception in alpha CGRP-deficient mice." *Nat. Neurosci.* 4: 357-358.
Schellenberger et al., (2009) "A recombinant polypeptide extends the in vivo half-life of peptides and proteins in a tunable manner " *Nature Biotechnology* 27 (12):1186-1192.
Shedden et al., (2001) "Efficacy and tolerability of timolol maleate ophthalmic gel-forming solution versus timolol ophthalmic solution in adults with open-angle glaucoma or ocular hypertension: a six-month, double-masked, multicenter study." *Clin. Ther.*, 23(3):440-50.
Shindo, et al. (2001) "Vascular Abnormalities and Elevated Blood Pressure in Mice Lacking Adrenomedullin Gene" *Circulation* 104:1964-1971.
Spatola, A.F. 1983 in: *Chemistry and Biochemistry of Amino Acids, Peptides, and Proteins*, B. Weinstein, eds., Marcel Dekker, New York, p. 267-357.
Tepper and Stillman (2008) "Clinical and Preclinical Rationale for CGRP-Receptor Antagonists in the Treatment of Migraine" *Headache* 48(8):1259-1268.
Tice and Bibi, in: *Treatise on Controlled Drug Delivery*, ed. A. Kydonieus, Marcel Dekker, N.Y. 1992, pp. 315-339.
Tilikaratne, et al. (2000) "Amylin Receptor Phenotypes Derived from Human Calcitonin Receptor/RAMP oexpression Exhibit Pharmacological Differences Dependent on Receptor Isoform and Host Cell Environment" *J. Pharmacol. Exp. Ther.* 294(1):61-72.
Weaner, et al. 1994 *Synthesis and Applications of Isotopically Labelled Compounds*, pp. 137-140.
Williamson, D.J. (2001) "Neurogenic inflammation in the context of migraine." *Microsc. Res. Tech.* 53:167-178.
Zhang et al. (2001) Arthritic calcitonin/alpha calcitonin gene-related peptide knockout mice have reduced nociceptive hypersensitivity. *Pain* 89:265-273.

* cited by examiner

```
                       SEQUENCE LISTING

<160> NUMBER OF SEQ ID NOS: 58

<210> SEQ ID NO 1
<211> LENGTH: 32
<212> TYPE: PRT
<213> ORGANISM: Artificial Sequence
<220> FEATURE:
<223> OTHER INFORMATION: Synthetic peptide

<400> SEQUENCE: 1

Ala Cys Asp Thr Ala Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Synthetic peptide

<400> SEQUENCE: 2

Ala Cys Asp Thr Ala Ser Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Synthetic peptide

<400> SEQUENCE: 3

Ala Cys Asp Thr Ala Val Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Synthetic peptide

<400> SEQUENCE: 4

Ala Cys Asn Thr Ala Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 5
```

<211> LENGTH: 32
<212> TYPE: PRT
<213> ORGANISM: Artificial Sequence
<220> FEATURE:
<223> OTHER INFORMATION: Synthetic peptide

<400> SEQUENCE: 5

Ala Cys Val Leu Gly Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Synthetic peptide

<400> SEQUENCE: 6

Ala Cys Arg Phe Gly Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Synthetic peptide

<400> SEQUENCE: 7

Ala Cys Asn Leu Ser Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Synthetic peptide

<400> SEQUENCE: 8

Cys Ser Asn Thr Ala Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Synthetic peptide

<400> SEQUENCE: 9

Ala Cys Asp Thr Ala Leu Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

```
<210> SEQ ID NO 10
<211> LENGTH: 32
<212> TYPE: PRT
<213> ORGANISM: Artificial Sequence
<220> FEATURE:
<223> OTHER INFORMATION: Synthetic peptide

<400> SEQUENCE: 10

Ala Cys Asp Thr Ala Ile Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Synthetic peptide

<400> SEQUENCE: 11

Ala Cys Asn Leu Ser Val Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Synthetic peptide

<400> SEQUENCE: 12

Cys Ser Asn Thr Ala Val Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 13

Ala Cys Asn Leu Ser Ala Cys Val Leu Gly Arg Leu Ser Gln Glu Leu
1               5                   10                  15

His Arg Leu Gln Thr Tyr Pro Thr Asn Thr Gly Ser Gly Thr Pro
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 14

Ala Cys Val Leu Gly Ala Cys Val Leu Gly Arg Leu Ser Gln Glu Leu
                5                   10                  15

His Arg Leu Gln Thr Tyr Pro Val Asp Pro Ser Ser Pro His Ser Tyr
            20                  25                  30
```

```
<210> SEQ ID NO 15
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 15

Ala Cys Asp Thr Ala Ala Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(1)
<223> OTHER INFORMATION: Xaa is selected from the group consisting of
      Ala, Cys, Gly, Ile, Leu, Met, Phe, Pro, Typ, and Val
<220> FEATURE:
<221> NAME/KEY: VARIANT
<222> LOCATION: (2)...(2)
<223> OTHER INFORMATION: Xaa is selected from the group consisting of
      Cys, Ser, and Tyr
<220> FEATURE:
<221> NAME/KEY: VARIANT
<222> LOCATION: (3)...(3)
<223> OTHER INFORMATION: Xaa is selected from the group consisting of
      Arg, Asn, Asp, Cys, Glu, Gln, His, Lys, Ser, Thr, Tyr, and Val
<220> FEATURE:
<221> NAME/KEY: VARIANT
<222> LOCATION: (4)...(4)
<223> OTHER INFORMATION: Xaa is selected from the group consisting of
      Arg, Asn, Asp, Cys, Glu, Gln, His, Leu, Lys, Phe, Ser, Thr, Tyr,
      and Val
<220> FEATURE:
<221> NAME/KEY: VARIANT
<222> LOCATION: (5)...(5)
<223> OTHER INFORMATION: is selected from the group consisting of Ala,
      Gly, Ile, Leu, Met, Phe, Ser, Typ, and Val
<220> FEATURE:
<221> NAME/KEY: VARIANT
<222> LOCATION: (6)...(6)
<223> OTHER INFORMATION: Xaa is selected from the group consisting of
      Ala, Cys, Asp, Glu, Phe, Gly, His, Ile, Lys, Leu, Met, Asn, Pro,
      Gln, Arg, Ser, Val, Trp, and Tyr

<400> SEQUENCE: 16

Xaa Xaa Xaa Xaa Xaa Xaa Cys
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Ala Cys Asp Thr Ala Ala Cys
1               5

<210> SEQ ID NO 18
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Ala Cys Asp Thr Ala Ser Cys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Ala Cys Asp Thr Ala Val Cys
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Ala Cys Asn Thr Ala Ala Cys
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Ala Cys Val Leu Gly Ala Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Ala Cys Arg Phe Gly Ala Cys
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Ala Cys Asp Leu Ser Ala Cys
1               5

<210> SEQ ID NO 24
<211> LENGTH: 7
```

```
<212> TYPE: PRT
<213> ORGANISM: Artificial Sequence
<220> FEATURE:
<223> OTHER INFORMATION: Synthetic Peptide

<400> SEQUENCE: 24

Ala Cys Asn Leu Ser Ala Cys
 1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Cys Ser Asn Thr Ala Ala Cys
 1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Ala Cys Asp Thr Ala Leu Cys
 1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Ala Cys Asp Thr Ala Ile Cys
 1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

Ala Cys Asp Thr Ala Leu Cys
 1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

Ala Cys Asp Thr Ala Ile Cys
 1               5

<210> SEQ ID NO 30
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 30

Ala Cys Asp Leu Ser Val Cys
 1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 31

Ala Cys Asp Leu Ser Val Cys
 1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Ala Cys Asn Leu Ser Val Cys
 1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Cys Ser Asn Thr Ala Val Cys
 1               5

<210> SEQ ID NO 34
<211> LENGTH: 19
<212> TYPE: PRT
<213> ORGANISM: Artificial Sequence
<220> FEATURE:
<223> OTHER INFORMATION: Synthetic peptide

<400> SEQUENCE: 34

Val Leu Gly Arg Leu Ser Gln Glu Leu His Arg Leu Gln Thr Tyr Pro
 1               5                  10                  15

Arg Thr Asn

<210> SEQ ID NO 35
<211> LENGTH: 19
<212> TYPE: PRT
<213> ORGANISM: Artificial Sequence
<220> FEATURE:
<223> OTHER INFORMATION: Synthetic peptide

<400> SEQUENCE: 35

Val Leu Gly Lys Leu Ser Gln Glu Leu His Lys Leu Gln Thr Tyr Pro
 1               5                  10                  15

Arg Thr Asn
```

```
<210> SEQ ID NO 36
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 36

Val Leu Gly Lys Leu Ser Gln Glu Leu His Lys Leu Gln Thr Tyr Pro
 1               5                   10                  15

Arg Thr Asn

<210> SEQ ID NO 37
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 37

Val Leu Gly Lys Leu Ser Gln Glu Leu His Lys Leu Gln Thr Tyr Pro
 1               5                   10                  15

Arg Thr Asp

<210> SEQ ID NO 38
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 38

Val Leu Gly Lys Leu Ser Gln Glu Leu His Lys Leu Gln Thr Phe Pro
 1               5                   10                  15

Arg Thr Asn

<210> SEQ ID NO 39
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 39

Val Leu Gly Lys Leu Ser Gln Asp Ile His Lys Leu Gln Thr Tyr Pro
 1               5                   10                  15

Arg Thr Asn

<210> SEQ ID NO 40
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 40

Val Leu Gly Lys Leu Ser Gln Glu Leu His Lys Met Gln Thr Tyr Pro
 1               5                   10                  15

Arg Thr Asp

<210> SEQ ID NO 41
<211> LENGTH: 19
<212> TYPE: PRT
<213> ORGANISM: Artificial Sequence
```

```
<220> FEATURE:
<223> OTHER INFORMATION: Synthetic Peptide

<400> SEQUENCE: 41

Leu Leu Gly Lys Leu Ser Gln Glu Leu His Arg Leu Gln Thr Tyr Thr
 1               5                  10                  15

Arg Thr Asp

<210> SEQ ID NO 42
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 42

Val Leu Gly Lys Leu Ser Gln Asp Leu His Lys Leu Gln Thr Phe Pro
 1               5                  10                  15

Arg Thr Asp

<210> SEQ ID NO 43
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 43

Met Leu Gly Lys Leu Ser Gln Asp Leu His Lys Leu Gln Thr Phe Pro
 1               5                  10                  15

Arg Thr Asp

<210> SEQ ID NO 44
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 44

Val Leu Gly Lys Leu Ser Gln Asp Ile His Lys Leu Gln Thr His Pro
 1               5                  10                  15

Arg Thr Asp

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(1)
<223> OTHER INFORMATION: Xaa is selected from the group consisting of
      Ala, Gly, Ile, leu, Met, Phe, Pro, Trp, and Val
<220> FEATURE:
<221> NAME/KEY: VARIANT
<222> LOCATION: (2)...(2)
<223> OTHER INFORMATION: Xaa is selected from the group consisting of
      Ala, Gly, Ile, leu, Met, Phe, Pro, Trp, and Val
<220> FEATURE:
<221> NAME/KEY: VARIANT
<222> LOCATION: (3)...(3)
<223> OTHER INFORMATION: Xaa is selected from the group consisting of
      Cys, Ser, and Tyr
<220> FEATURE:
<221> NAME/KEY: VARIANT
```

```
<222> LOCATION: (4)...(4)
<223> OTHER INFORMATION: Xaa is selected from the group consisting of
      Arg, Asn, Asp, Glu, Gln, His, Lys, Ser, Thr, and Tyr
<220> FEATURE:
<221> NAME/KEY: VARIANT
<222> LOCATION: (5)...(5)
<223> OTHER INFORMATION: Xaa is selected from the group consisting of
      Ala, Gly, Ile, leu, Met, Phe, Pro, Trp, and Val
<220> FEATURE:
<221> NAME/KEY: VARIANT
<222> LOCATION: (6)...(6)
<223> OTHER INFORMATION: Xaa is selected from the group consisting of
      Ala, Gly, Ile, leu, Met, Phe, Pro, Trp, and Val

<400> SEQUENCE: 45

Xaa Xaa Xaa Xaa Xaa Xaa
 1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide

<400> SEQUENCE: 46

Val Gly Ser Lys Ala Phe
 1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide

<400> SEQUENCE: 47

Val Gly Ser Lys Ala Phe
 1               5

<210> SEQ ID NO 48
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 48

Val Leu Gly Arg Leu Ser Gln Glu Leu His Arg Leu Gln Thr Tyr Pro
 1               5                  10                  15

Arg Thr Asn

<210> SEQ ID NO 49
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 49

Val Leu Gly Lys Leu Ser Gln Glu Leu His Lys Leu Gln Thr Tyr Pro
 1               5                  10                  15

Arg Thr Asn

<210> SEQ ID NO 50
<211> LENGTH: 7
<212> TYPE: PRT
```

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)...(6)
<223> OTHER INFORMATION: Xaa = any amino acid residue other than Thr

<400> SEQUENCE: 50

Ala Cys Asp Thr Ala Xaa Cys
 1               5

<210> SEQ ID NO 51
<211> LENGTH: 17
<212> TYPE: PRT
<213> ORGANISM: Artificial Sequence
<220> FEATURE:
<223> OTHER INFORMATION: Synthetic peptide

<400> SEQUENCE: 51

Ala Glu Ala Ala Ala Lys Glu Ala Ala Ala Lys Glu Ala Ala Ala Lys
 1               5                  10                  15

Ala

<210> SEQ ID NO 52
<211> LENGTH: 17
<212> TYPE: PRT
<213> ORGANISM: Artificial Sequence
<220> FEATURE:
<223> OTHER INFORMATION: Synthetic peptide

<400> SEQUENCE: 52

Ala Lys Ala Ala Ala Glu Lys Ala Ala Ala Glu Lys Ala Ala Ala Glu
 1               5                  10                  15

Ala

<210> SEQ ID NO 53
<211> LENGTH: 16
<212> TYPE: PRT
<213> ORGANISM: Artificial Sequence
<220> FEATURE:
<223> OTHER INFORMATION: Synthetic peptide

<400> SEQUENCE: 53

Ala Glu Ala Ala Lys Ala Glu Ala Ala Lys Glu Ala Ala Lys Ala
 1               5                  10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic peptide

<400> SEQUENCE: 54

Ala Lys Ala Ala Glu Ala Lys Ala Ala Glu Ala Lys Ala Ala Glu Ala
 1               5                  10                  15

<210> SEQ ID NO 55
<211> LENGTH: 25
<212> TYPE: PRT
<213> ORGANISM: Artificial Sequence
<220> FEATURE:
<223> OTHER INFORMATION: Synthetic peptide

<400> SEQUENCE: 55

```
Val Leu Gly Lys Leu Ser Gln Glu Leu His Lys Leu Gln Thr Tyr Pro
1               5                   10                  15

Arg Thr Asn Thr Gly Ser Asn Thr Tyr
            20                  25

<210> SEQ ID NO 56
<211> LENGTH: 37
<212> TYPE: PRT
<213> ORGANISM: Artificial Sequence
<220> FEATURE:
<223> OTHER INFORMATION: Synthetic peptide

<400> SEQUENCE: 56

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 57
<211> LENGTH: 32
<212> TYPE: PRT
<213> ORGANISM: Artificial Sequence
<220> FEATURE:
<223> OTHER INFORMATION: Synthetic peptide

<400> SEQUENCE: 57

Ala Cys Asp Leu Ser Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Synthetic peptide

<400> SEQUENCE: 58

Ala Cys Asp Leu Ser Val Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30
```

PEPTIDE ANTAGONISTS OF THE CALCITONIN CGRP FAMILY OF PEPTIDE HORMONES AND THEIR USE

CROSS REFERENCE TO RELATED APPLICATIONS

This application claims priority to U.S. Provisional Patent Application 61/591,236 filed on Jan. 26, 2012 and entitled "PEPTIDE ANTAGONISTS OF THE CALCITONIN CGRP FAMILY OF PEPTIDE HORMONES AND THEIR USE," the entirety of which is hereby incorporated by reference herein.

SEQUENCE LISTING

The present application is being filed along with a sequence listing in Electronic format. The Sequence Listing is provided as a file entitled CSOAR-001NP Substitute.txt, created Nov. 18, 2014 which is approximately 17 kb in size. The information in the electronic format of the sequence listing is incorporated herein by reference in its entirety in its entirety.

BACKGROUND OF THE INVENTION

1. Field of the Invention

The present embodiments relate to peptide antagonists of the calcitonin/calcitonin gene-related peptide (CT/CGRP) family of peptide hormones and therapeutic uses thereof.

2. Description of the Related Art

The CT/CGRP peptide family includes calcitonin gene-related peptide (CGRP), adrenomedullin (ADM), intermedin (IM), calcitonin (CT) and amylin. The biological actions of these peptides are mediated via binding to two closely related type II G protein-coupled receptors, the calcitonin receptor (CTR) and the calcitonin receptor-like receptor (CRLR) (Christopoulos, et al. 1999, *Mol. Pharmacol.* 56:235-242; Poyner et al. 2002 *Pharmacol. Rev.* 54:233-246). Although the calcitonin receptor is the main mediator for calcitonin action, it preferentially binds amylin, when the receptor is associated with a receptor activity modifying protein (RAMP) (see, e.g., Tilikaratne, et al. 2000, *J. Pharmacol. Exp. Ther.* 294(1):61-72). Cloning and functional studies have shown that CGRP, ADM, IM and, to a lesser extent, amylin likewise interact with different combinations of CRLR and the three receptor activity modifying proteins (RAMP-1, RAMP-2 and RAMP-3); see, e.g., McLatchie et al. 1998, *Nature* 393:333-339 and Roh et al. 2004, *JBC* 279 (8):7264-7274). In fact, co-expression of the calcitonin receptor-like receptor (CRLR) and receptor activity-modifying proteins (RAMPs) is required to generate functional receptors for calcitonin gene-related peptide (CGRP), adrenomedullin (ADM) and intermedin (IM). The formation of heterodimers between RAMPs and CRLR is essential for the proper cell surface targeting and pharmacological characteristics of CGRP, ADM and IM receptors. Co-expression of RAMP-1 with CRLR leads to the formation of a CGRP receptor, whereas RAMP-2 and RAMP-3 co-expression with CRLR form ADM and IM receptors respectively (Miret, et al. 2002, *JBC* 277(9):6881-6887.) IM has been shown to be a nonselective agonist for all three RAMP/CRLR co-receptors.

The physiological functions of the hormone peptides in the CT/CGRP family are determined by receptor-binding specificity and the tissue expression profiles of individual ligands and their respective receptors and have been shown to be involved in cardiovascular morphogenesis, sensory neurotransmission, inflammatory reactions, nociceptive behavior and glucose homeostasis (see, e.g., Hay, et al. 2001, *Trends Pharmacol. Sci.* 22:57-59; Shindo, et al. 2001, *Circulation* 104:1964-1971; Zhang et al. 2001, *Pain* 89:265-273; Salmon et al. (1999) *Neuroreport* 10:849-854; Salmon, et al. 2001, *Nat. Neurosci.* 4: 357-358; and Mulder, et al. 2000, *Am. J. Physiol.* 278:E684-E691).

CGRP (calcitonin gene-related peptide), a well-studied peptide in the CT/CGRP family of peptide hormones, is a sensory neuropeptide with potent vasodilatory and cardiotonic action as described in U.S. Pat. No. 4,530,838 to Evans, et al. CGRP is present in both the central and peripheral nervous systems and is concentrated in those areas of the body receiving sensory input from the dorsal horn with limited amounts associated with autonomic input. In the brain, the peptide is present in the nuclei of sensory and motor cranial nerves and in cell bodies in the hypothalamus, preoptic area, ventromedial thalamus, hippocampus, and the like (Poyner, D. 1992, *Pharmac. Ther.* 56:23-51).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has particularly been implicated in the pathogenesis of migraine headache (Edvinsson L. 2001, *CNS Drugs* 15(10):745-53; Williamson, D. J. 2001 *Microsc. Res. Tech.* 53:167-178; Grant, A. D. 2002, *Brit. J Pharmacol.* 135:356-362). Migraines are noted for the strength of the headache that ensues with its pathology. It is believed that the headache associated with migraines results from the profound cerebral vasodilation associated with migraine events. CGRP-containing nerve fibers innervate cerebral and dural vessels where CGRP is believed to prolong vasodilation. (Moskowitz 1992, *Trends Pharmacol. Sci.* 13:307-311). Further, serum levels of CGRP are elevated during migraine (Goadsby, et al. 1990, *Ann. Neurol.* 28:183-7), and treatment with anti-migraine drugs returns CGRP levels to normal coincident with alleviation of headache (Gallai, et al. 1995, *Cephalalgia* 15:384-90). Migraineurs exhibit elevated basal CGRP levels compared to controls (Ashina, et al., 2000, *Pain* 86(1-2)133-8). Intravenous CGRP infusion produces lasting headache in migraineurs (Lassen, et al. 2002, *Cephalalgia* 22(1):54-61). Thus, CGRP antagonists have been the focus of recent research as a method for blocking cerebrovascular CGRP receptors and thus blocking the vasodilation causing migraine.

Both small molecule and peptide antagonists of the CGRP receptor are known. These include, for example, intravenous olcegepant (BIBN4096 BS) and oral telcagepant (MK-0974), produced by Boehringer Ingelheim Pharmaceuticals and Merck & Co., Inc., respectively. Both of these small molecule CGRP antagonists have been shown to be safe, effective and well tolerated in early clinical trials for the acute treatment of migraines. (See, e.g., Tepper and Stillman, 2008, *Headache* 48(8):1259-1268; and Durham and Vause 2010, *CNS Drugs* 24(7):539-548.) However, recently a Phase II investigation into the use of the small molecule CGRP antagonist, MK-3207, to prevent migraines was discontinued by Merck & Co., Inc. due to observance of asymptomatic liver test abnormalities in some patients in an extended Phase I pharmacology study ("Merck Updates Status of Clinical Development Programs for Investigational CGRP Receptor Antagonist Treatments for Acute Migraine; MK-3207 Clinical Development Discontinued." Sep. 10, 2009. Merck & Co., Inc. Web. Jun. 1, 2011).

Other molecules known to compete for the CGRP receptor are peptides comprising the sequence of CGRP but lacking at least the first seven amino acids of the CGRP amino acid sequence, for example, including, but not limited to, CGRP (8-37), CGRP (28-37), [Tyr⁰]CGRP (28-37), and CGRP (12-37). Other CGRP antagonists include h-α-CGRP (9-37), h-α-CGRP (10-37), h-α-CGRP (11-37) (Mimeault, M. et al., 1992, *J. Med. Chem.* 35; 2163-2168). Still other CGRP antagonists include [Ala$^9$]-h-α-CGRP (8-37), [Ala$^{10}$]-h-α-CGRP (8-37), [Ala$^{11}$]-h-α-CGRP (8-37), and [Ala$^{12}$]-h-α-CGRP (8-37), id. Additional CGRP antagonists include h-α-CGRP (19-37), h-α-CGRP (23-37) and acetyl-h-α-CGRP (19-37) (Rovero, P. et al. 1992, *Peptides* 13:1025-1027).

While a number of CGRP receptor peptide antagonists have been shown to effectively compete with CGRP in vitro, these antagonists have not performed as well in in vivo models of migraine-like pathologies.

SUMMARY OF THE INVENTION

It has been surprisingly found that certain select amino acids in the N-terminal portion of the calcitonin gene-related peptide, as disclosed and described herein, are responsible for the peptide agonist activity. Further, substituting certain amino acids in the N-terminal portion of the calcitonin gene-related peptide can tune the activity from an agonist to an antagonist. Further still, it has been discovered that additional substitutions or modifications can provide additional desirable characteristics to the antagonists of the present invention.

Some embodiments provide a modified calcitonin gene-related peptide antagonist, said antagonist having the structure of Formula I:

$$X^1\text{-}Y^1\text{-}Z^1 \quad (I)$$

wherein:
- $X^1$ is an N-terminal fragment of a modified calcitonin gene-related peptide or other CT/CGRP peptide family member comprising at least five to seven amino acid residues, where two amino acid residues of the N-terminal fragment are cysteine (Cys), wherein the final residue is Cys, and wherein the residue immediately preceding the final Cys residue is a non-threonine substitution of a threonine (Thr) residue;
- $Y^1$ is a central core comprising 15 to more than 24, 15 to 24, 15 to 22, 18-22, or 19-20 residues where at least some of the residues of the central core are capable of forming an α-helix under physiological conditions, wherein at least one amino acid of the central core is arginine (Arg) or lysine (Lys) and the central core comprises an α-helix; and
- $Z^1$ is a modified C-terminal fragment of modified calcitonin gene-related peptide or other CT/CGRP peptide family member comprising from five to seven amino acid residues with a C-terminal amide, where at least one amino acid residue of the C-terminal fragment is phenylalanine (Phe) tyrosine (Tyr), proline (Pro) or hydroxyproline (Hyp);

or pharmaceutically acceptable salt thereof.

Some embodiments provide a modified calcitonin gene-related peptide antagonist, comprising:
an amino acid sequence having at least 80% sequence identity to the amino acid sequence of SEQ ID NOS: 1, 2, 3, 4, 5, 6, 7, 8, 9, 10, 11, 12, 13, 14 or 15 wherein said peptide retains antagonist activity.

Some embodiments provide a pharmaceutical composition comprising a pharmaceutically acceptable excipient and a modified calcitonin gene-related peptide antagonist as disclosed and described herein.

Some embodiments provide a method of treating a condition associated with aberrant levels of CGRP comprising the administration of a modified calcitonin gene-related peptide antagonist as disclosed and described herein, to an individual, the method comprising administering to the individual an effective amount of a modified calcitonin gene-related peptide antagonist as disclosed and described herein.

Some embodiments provide a modified calcitonin gene-related peptide antagonist having the structure selected from the following peptide sequences, listed in Table 1.

TABLE 1

| Sequence | SEQ ID |
|---|---|
| NH$_2$-ACDTAACVLGRLSQELHRLQTYPRTNVGSKAF-NH$_2$; | (SEQ ID NO: 1)-NH$_2$ |
| NH$_2$-ACDTASCVLGRLSQELHRLQTYPRTNVGSKAF-NH$_2$; | (SEQ ID NO: 2)-NH$_2$ |
| NH$_2$-ACDTAVCVLGRLSQELHRLQTYPRTNVGSKAF-NH$_2$; | (SEQ ID NO: 3)-NH$_2$ |
| NH$_2$-ACNTAACVLGRLSQELHRLQTYPRTNVGSKAF-NH$_2$; | (SEQ ID NO: 4)-NH$_2$ |
| NH$_2$-ACVLGACVLGRLSQELHRLQTYPRTNVGSKAF-NH$_2$; | (SEQ ID NO: 5)-NH$_2$ |
| NH$_2$-ACRFGACVLGRLSQELHRLQTYPRTNVGSKAF-NH$_2$; | (SEQ ID NO: 6)-NH$_2$ |
| NH$_2$-ACNLSACVLGRLSQELHRLQTYPRTNVGSKAF-NH$_2$; | (SEQ ID NO: 7)-NH$_2$ |
| NH$_2$-CSNTAACVLGRLSQELHRLQTYPRTNVGSKAF-NH$_2$; | (SEQ ID NO: 8)-NH$_2$ |
| NH$_2$-ACDTALCVLGRLSQELHRLQTYPRTNVGSKAF-NH$_2$; | (SEQ ID NO: 9)-NH$_2$ |
| NH$_2$-ACDTAICVLGRLSQELHRLQTYPRTNVGSKAF-NH$_2$; | (SEQ ID NO: 10)-NH$_2$ |
| NH$_2$-ACNLSVCVLGRLSQELHRLQTYPRTNVGSKAF-NH$_2$; | (SEQ ID NO: 11)-NH$_2$ |
| NH$_2$-CSNTAVCVLGRLSQELHRLQTYPRTNVGSKAF-NH$_2$; | (SEQ ID NO: 12)-NH$_2$ |
| NH$_2$-ACNLSACVLGRLSQELHRLQTYPTNTGSGTP-NH$_2$; | (SEQ ID NO: 13)-NH$_2$ |
| NH$_2$-ACVLGACVLGRLSQELHRLQTYPVDPSSPHSY-NH$_2$; or | (SEQ ID NO: 14)-NH$_2$ |
| NH$_2$-ACDTAACVTHRLAGLLSRSGGVVKNNFVPTNVGSKAF-NH$_2$ | (SEQ ID NO: 15)-NH$_2$ |

Some embodiments provide a method for delivering a therapeutic agent to a cell. The therapeutic agent is linked to a modified calcitonin gene-related peptide antagonist as disclosed and described herein that selectively binds to member of the CGRP receptor family.

Some embodiments provide a conjugate which comprises a therapeutic agent linked to a modified calcitonin gene-related peptide antagonist as disclosed and described herein that selectively binds to a member of the CGRP receptor family. Some embodiments provide a method of identifying a CGRP receptor binding ligand by providing a modified calcitonin gene-related peptide antagonist bound to a CGRP receptor, providing a test compound or library of test compounds, and identifying compounds which are capable of dissociating the calcitonin gene-related peptide antagonist from the CGRP receptor. Such compounds identified by this method may be further screened against other CGRP receptors and CGRP receptor binding agents to identify selective CGRP receptor binding ligands.

DETAILED DESCRIPTION OF THE PREFERRED EMBODIMENT

Some embodiments provide a modified calcitonin gene-related peptide antagonist, said antagonist having the structure of Formula I:

$$X^1\text{-}Y^1\text{-}Z^1 \quad (I)$$

wherein:
- $X^1$ is a modified N-terminal fragment of calcitonin gene-related peptide other CT/CGRP peptide family member comprising from five to seven amino acid residues, wherein two amino acid residues of the N-terminal fragment are cysteine (Cys), wherein the C-terminal residue of the fragment is Cys, and wherein the residue immediately preceding the C-terminal Cys residue of the fragment is a non-threonine substitution of a threonine (Thr) residue;
- $Y^1$ is a central core wherein at least one amino acid of the central core is arginine (Arg) or lysine (Lys) and the central core comprises an α-helix; and
- $Z^1$ is a modified C-terminal fragment of calcitonin gene-related peptide or other CT/CGRP peptide family member comprising from five to seven amino acid residues with a C-terminal amide, where at least one amino acid of the C-terminal fragment is phenylalanine (Phe), tyrosine (Tyr), proline (Pro) or hydroxyproline (Hyp), or pharmaceutically acceptable salt thereof.

In some embodiments, X1 has the characteristics that a residue which precedes the C-terminal Cysteine by four, five or six amino acid positions is also a Cysteine, such that the two aforementioned Cysteines can form a disulfide bond. Residues between the two Cys residues involved in the disulfide bond are unconstrained in sequence except that the residue preceding the C-terminal Cys residue of the fragment must not be a Thr, as mentioned above, and that there may not be more than two cysteines in the C-terminal 7 residues of the X1 fragment. The aforementioned disulfide bond stabilizes the structure of X1, facilitating both formation of the alpha-helix in Y1, below, and binding of X1 to the transmembrane component of a target receptor in competition with CGRP.

Introduction of a residue other than Thr at the position immediately N-terminal to the second cysteine in the $X^1$ fragment above results in a loss of the activation activity of the molecule in interactions with a CGRP receptor or with a member of the CT/CGRP family of receptors as compared to the wild-type molecule which has a Thr at said position, but may not affect the binding to the receptor. As a result, such substitutions yield a molecule which can occupy the receptor, but which antagonizes rather than activates the signal transduction pathway by making the receptor unavailable for binding by signal-transducing agonists.

Addition of residues N-terminal to $X^1$ may not impact the activity of the antagonist in some embodiments. In some embodiments addition of residues N-terminal to $X^1$, for example an 864 residue XTENS sequence comprising Ala, Glu, Gly, Pro, Ser and Thr, may affect the stability of the drug (Schellenberger et al., 2009, *Nature Biotechnology* 27 (12): 1186-1192). In some embodiments the addition of residues N-terminal may increase the half-life of an administered drug. These changes are contemplated herein; a person having ordinary skill in the art will know how this can be done.

In some embodiments the antagonist as disclosed herein comprises a central core $Y^1$ comprising 15 to 22 residues. In some embodiments the antagonist as disclosed herein comprises a central core $Y^1$ comprising more than 24, 15 to 24, 15 to 22, 18-22, or 19-20 residues where at least some of the residues of the central core are capable of forming an α-helix under physiological conditions. The fourth residue from the N-terminus of this central core is frequently a positively charged residue, either Arginine (Arg) or Lysine (Lys). The eighteenth residue is frequently Arginine. The length of the central core is constrained not by the number of residues per se but by the steric considerations that require $X^1$ and $Z^1$ to be positioned so that they may interact with a target receptor at the cell membrane surface and at an extracellular domain, respectively, in competition with CGRP.

$Z^1$ is a modified C-terminal fragment of a modified calcitonin gene-related peptide or other CT/CGRP peptide family member comprising from five to seven amino acid residues or more, with a C-terminal amide, and wherein at least one amino acid of the C-terminal fragment can be phenylalanine (Phe), proline (Pro), tyrosine (Tyr), or hydroxyproline (Hyp). Like $Y^1$ above, $Z^1$ is constrained not by its sequence but by a functional requirement. In the case of $Z^1$ that requirement is that it interact with a target receptor at a site in its extracellular domain such that when the antagonist binds the CGRP receptor, in competition with CGRP, $X^1$ is positioned to interact with the receptor at the cell surface and $Z^1$ interacts with a RAMP portion of the receptor.

The full peptide may be delivered alone or as a pharmaceutically acceptable salt thereof.

Some embodiments provide a calcitonin gene-related peptide antagonist, comprising:
- an amino acid sequence having at least 80% sequence identity to the amino acid sequence of SEQ ID NOS: 1, 2, 3, 4, 5, 6, 7, 8, 9, 10, 11, 12, 13, 14 or 15 wherein said peptide retains antagonist activity.

Some embodiments comprise an antagonist with a core region of 18-22 residues.

In some embodiments of the modified calcitonin gene-related peptide antagonist having the structure of Formula I, the N-terminal fragment comprises:

$X^{11}$-$X^{12}$-$X^{13}$-$X^{14}$-$X^{15}$-$X^{16}$-$X^{17}$ (SEQ ID NO: 16), where:
- $X^{11}$ can be selected from the group consisting of alanine (Ala), cysteine (Cys), glycine (Gly), isoleucine (Ile), leucine (Leu), methionine (Met), phenylalanine (Phe), proline (Pro), tryptophan (Trp), and valine (Val);
- $X^{12}$ can be selected from the group consisting of cysteine (Cys), serine (Ser), and tyrosine (Tyr);
- $X^{13}$ can be selected from the group consisting of arginine (Arg), asparagine (Asn), aspartic acid (Asp), cysteine (Cys), glutamic acid (Glu), glutamine (Gln), histidine (His), lysine (Lys), serine (Ser), threonine (Thr), tyrosine (Tyr), and valine (Val);
- $X^{14}$ can be selected from the group consisting of arginine (Arg), asparagine (Asn), aspartic acid (Asp), glutamic acid (Glu), glutamine (Gln), histidine (His), leucine (Leu), lysine (Lys), phenylalanine (Phe), serine (Ser), threonine (Thr), tyrosine (Tyr), and valine (Val);
- $X^{15}$ can be selected from the group consisting of alanine (Ala), glycine (Gly), isoleucine (Ile), leucine (Leu), methionine (Met), phenylalanine (Phe), serine (Ser), tryptophan (Typ), and valine (Val);
- $X^{16}$ can be selected from the group consisting of alanine (Ala), glycine (Gly), isoleucine (Ile), leucine (Leu), methionine (Met), phenylalanine (Phe), serine (Ser), tryptophan (Typ), and valine (Val); and $X^{17}$ is cysteine (Cys), and is capable of forming a disulfide bridge with a cysteine residue in $X^{11}$, $X^{12}$, or $X^{13}$; and with the further limitation that only two residues of $X^1$ (that is, $X^{17}$ and only one of $X^{11}$, $X^{12}$, and $X^{13}$) are cysteine residues.

In some embodiments of the modified calcitonin gene-related peptide antagonist having the structure of Formula I, $X^{11}$ is selected from the group consisting of Ala, Cys, and Gly. In some embodiments of the modified calcitonin gene-related peptide antagonist having the structure of Formula I, $X^{12}$ is selected from the group consisting of Cys and Ser, with the caveat that only one of $X^{11}$ and $X^{12}$ can be Cys. In some embodiments of the modified calcitonin gene-related peptide antagonist having the structure of Formula I, $X^{13}$ is selected from the group consisting of Arg, Asn, Asp, and Val. In some embodiments of the modified calcitonin gene-related peptide antagonist having the structure of Formula I, $X^{14}$ is selected from the group consisting of Leu, Phe, and Thr. In some embodiments of the modified calcitonin gene-related peptide antagonist having the structure of Formula I, $X^{15}$ is selected from the group consisting of Ala, Gly, and Ser. In some embodiments of the modified calcitonin gene-related peptide antagonist having the structure of Formula I, $X^{15}$ is selected from the group consisting of Ala, Ile, Leu, Ser, and Val.

In some embodiments of the modified calcitonin gene-related peptide antagonist having the structure of Formula I, $X^{11}$-$X^{12}$-$X^{13}$-$X^{14}$-$X^{15}$-$X^{16}$-$X^{17}$ is selected from the group consisting of $NH_2$-Ala-Cys-Asp-Thr-Ala-Ala-Cys (SEQ ID NO: 17), $NH_2$-Ala-Cys-Asp-Thr-Ala-Ser-Cys (SEQ ID NO: 18), $NH_2$-Ala-Cys-Asp-Thr-Ala-Val-Cys (SEQ ID NO: 19), $NH_2$-Ala-Cys-Asn-Thr-Ala-Ala-Cys (SEQ ID NO: 20), $NH_2$-Ala-Cys-Val-Leu-Gly-Ala-Cys (SEQ ID NO: 21), $NH_2$-Ala-Cys-Arg-Phe-Gly-Ala-Cys (SEQ ID NO: 22), $NH_2$-Ala-Cys-Asp-Leu-Ser-Ala-Cys (SEQ ID NO: 23), $NH_2$-Ala-Cys-Asn-Leu-Ser-Ala-Cys (SEQ ID NO: 24), $NH_2$-Cys-Ser-Asn-Thr-Ala-Ala-Cys (SEQ ID NO: 25), $NH_2$-Ala-Cys-Asp-Thr-Ala-Leu-Cys (SEQ ID NO: 26), $NH_2$-Ala-Cys-Asp-Thr-Ala-Ile-Cys (SEQ ID NO: 27), $NH_2$-Ala-Cys-Asp-Thr-Ala-Leu-Cys (SEQ ID NO: 28), $NH_2$-Ala-Cys-Asp-Thr-Ala-Ile-Cys (SEQ ID NO: 29), $NH_2$-Ala-Cys-Asp-Leu-Ser-Val-Cys (SEQ ID NO: 30), $NH_2$-Ala-Cys-Asp-Leu-Ser-Val-Cys (SEQ ID NO: 31), $NH_2$-Ala-Cys-Asn-Leu-Ser-Val-Cys (SEQ ID NO: 32), and $NH_2$-Cys-Ser-Asn-Thr-Ala-Val-Cys (SEQ ID NO: 33).

In some embodiments, one or more residues are fused N-terminally to $X^{11}$, thereby generating a polypeptide with an N-terminal extension of residues with respect to $X^1$. In some embodiments this extension affects the stability of the antagonist after administration.

In some embodiments of the modified calcitonin gene-related peptide antagonist having the structure of Formula I, the central core comprises a fragment of human or salmon calcitonin. In some embodiments, the fragment of human or salmon calcitonin comprises 18 to 21 amino acids. In some embodiments the fragment of human or salmon calcitonin comprises 18 to 20 amino acids. In some embodiments of the modified calcitonin gene-related peptide antagonist having the structure of Formula I, $Y^1$ comprises 19 to 20 amino acids. In some embodiments of the modified calcitonin gene-related peptide antagonist having the structure of Formula I, $Y^1$ is -Val-Leu-Gly-Arg-Leu-Ser-Gln-Glu-Leu-His-Arg-Leu-Gln-Thr-Tyr-Pro-Arg-Thr-Asn- (SEQ ID NO: 34) or -Val-Leu-Gly-Lys-Leu-Ser-Gln-Glu-Leu-His-Lys-Leu-Gln-Thr-Tyr-Pro-Arg-Thr-Asn- (SEQ ID NO: 35). In some embodiments of the modified calcitonin gene-related peptide antagonist having the structure of Formula I, $Y^1$ has 95% sequence identity with -Val-Leu-Gly-Arg-Leu-Ser-Gln-Glu-Leu-His-Arg-Leu-Gln-Thr-Tyr-Pro-Arg-Thr-Asn- (SEQ ID NO: 34) or -Val-Leu-Gly-Lys-Leu-Ser-Gln-Glu-Leu-His-Lys-Leu-Gln-Thr-Tyr-Pro-Arg-Thr-Asn- (SEQ ID NO: 35).

In some embodiments of the modified calcitonin gene-related peptide antagonist having the structure of Formula I, the central core comprises a fragment of a calcitonin from any of a range of species. In some embodiments, $Y^1$ can have a 60%, 65%, 70%, 75%, 80%, 85%, 90%, or 95% sequence identity with the $Y^1$ of SEQ ID 34 (Val-Leu-Gly-Arg-Leu-Ser-Gln-Glu-Leu-His-Arg-Leu-Gln-Thr-Tyr-Pro-Arg-Thr-Asn-). In some embodiments of the calcitonin gene-related peptide antagonist having the structure of Formula I, $Y^1$ can be -Val-Leu-Gly-Lys-Leu-Ser-Gln-Glu-Leu-His-Lys-Leu-Gln-Thr-Tyr-Pro-Arg-Thr-Asn- (SEQ ID NO: 35) or -Val-Leu-Gly-Lys-Leu-Ser-Gln-Glu-Leu-His-Lys-Leu-Gln-Thr-Tyr-Pro-Arg-Thr-Asp- (SEQ ID NO: 36) or -Val-Leu-Gly-Lys-Leu-Ser-Gln-Glu-Leu-His-Lys-Leu-Gln-Thr-Phe-Pro-Arg-Thr-Asn- (SEQ ID NO: 37) or -Val-Leu-Gly-Lys-Leu-Ser-Gln-Asp-Ile-His-Lys-Leu-Gln-Thr-Tyr-Pro-Arg-Thr-Asn- (SEQ ID NO: 38) or -Val-Leu-Gly-Lys-Leu-Ser-Gln-Glu-Leu-His-Lys-Met-Gln-Thr-Tyr-Pro-Arg-Thr-Asp- (SEQ ID NO: 39) or -Leu-Leu-Gly-Lys-Leu-Ser-Gln-Glu-Leu-His-Arg-Leu-Gln-Thr-Tyr-Thr-Arg-Thr-Asp- (SEQ ID NO: 40) or -Val-Leu-Gly-Lys-Leu-Ser-Gln-Asp-Leu-His-Lys-Leu-Gln-Thr-Phe-Pro-Arg-Thr-Asp- (SEQ ID NO: 41) or -Met-Leu-Gly-Lys-Leu-Ser-Gln-Asp-Leu-His-Lys-Leu-Gln-Thr-Phe-Pro-Arg-Thr-Asp- (SEQ ID NO: 42) or -Val-Leu-Gly-Lys-Leu-Ser-Gln-Asp-Ile-His-Lys-Leu-Gln-Thr-His-Pro-Arg-Thr-Asp- (SEQ ID NO: 43). In some embodiments, $Y^1$ can have a 60% or greater sequence identity with any of the $Y^1$ of the sequences immediately above.

Some embodiments provide $Y^1$ polypeptides that have at least about 60% amino acid sequence identity, alternatively at least about 61% amino acid sequence identity, alternatively at least about 62% amino acid sequence identity, alternatively at least about 63% amino acid sequence identity, alternatively at least about 64% amino acid sequence identity, alternatively at least about 65% amino acid sequence identity, alternatively at least about 66% amino acid sequence identity, alternatively at least about 67% amino acid sequence identity, alternatively at least about 68% amino acid sequence identity, alternatively at least about 69% amino acid sequence identity, alternatively at least about 70% amino acid sequence identity, alternatively at least about 71% amino acid sequence identity, alternatively at least about 72% amino acid sequence identity, alternatively at least about 73% amino acid sequence identity, alternatively at least about 74% amino acid sequence identity, alternatively at least about 75% amino acid sequence identity, alternatively at least about 76% amino acid sequence identity, alternatively at least about 77% amino acid sequence identity, alternatively at least about 78% amino acid sequence identity, alternatively at least about 79% amino acid sequence identity, alternatively at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a $Y^1$ polypeptide fragment listed above.

In some embodiments of the modified calcitonin gene-related peptide antagonist having the structure of Formula, I, $Z^1$ comprises $Z^{11}$-$Z^{12}$-$Z^{13}$-$Z^{14}$-$Z^{15}$-$Z^{16}$ (SEQ ID NO: 45) where:

$Z^{11}$ is selected from the group consisting of Ala, Gly, Ile, Leu, Met, Phe, Pro, Trp, and Val;

$Z^{12}$ is selected from the group consisting of Ala, Gly, Ile, Leu, Met, Phe, Pro, Trp, and Val;

$Z^{13}$ is selected from the group consisting of serine (Ser), and tyrosine (Tyr);

$Z^{14}$ is selected from the group consisting of Arg, Asn, Asp, Glu, Gln, His, Lys, Ser, Thr, and Tyr;

$Z^{15}$ is selected from the group consisting of Ala, Gly, Ile, Leu, Met, Phe, Pro, Trp, and Val; and $Z^{16}$ is selected from the group consisting of Ala, Gly, Ile, Leu, Met, Phe, Pro, Trp, and Val. In some embodiments, $Z^{11}$ is Val. In some embodiments, $Z^{12}$ is Gly. In some embodiments, $Z^{13}$ is Ser. In some embodiments, $Z^{14}$ is Lys. In some embodiments, $Z^{15}$ is Ala. In some embodiments, $Z^{16}$ is Phe. In some embodiments, $Z^{11}$-$Z^{12}$-$Z^{13}$-$Z^{14}$-$Z^{15}$-$Z^{16}$ is -Val-Gly-Ser-Lys-Ala-Phe such that the C-terminus of the polypeptide is a carboxy moiety (SEQ ID NO: 46), or -Val-Gly-Ser-Lys-Ala-Phe-NH$_2$, such that the C-terminus of the polypeptide is a carboxamide moiety (SEQ ID NO: 47).

In some embodiments the C-terminal residue of $Z^1$ is Phenylalanine, Tyrosine, Proline or Hydroxyproline. In some embodiments the C-terminal residue of $Z^1$ is Phenylalanine.

In some embodiments $Z^1$ comprises at least one Phe residue.

In some embodiments the C-terminus of $Z^1$ is modified so that it is bounded by an amidated carboxy (—C(=O)NH$_2$) moiety.

In some embodiments of the modified calcitonin gene-related peptide antagonist having the structure of Formula I, $X^1$ is selected from the group consisting of NH$_2$-Ala-Cys-Asp-Thr-Ala-Ala-Cys- (SEQ ID NO: 17), NH$_2$-Ala-Cys-Asp-Thr-Ala-Ser-Cys- (SEQ ID NO: 18), NH$_2$-Ala-Cys-Asp-Thr-Ala-Val-Cys- (SEQ ID NO: 19), NH$_2$-Ala-Cys-Asn-Thr-Ala-Ala-Cys- (SEQ ID NO: 20), NH$_2$-Ala-Cys-Val-Leu-Gly-Ala-Cys-, NH$_2$-Ala-Cys-Arg-Phe-Gly-Ala-Cys- (SEQ ID NO: 21), NH$_2$-Ala-Cys-Arg-Phe-Gly-Ala-Cys- (SEQ ID NO: 22), NH$_2$-Ala-Cys-Asp-Leu-Ser-Ala-Cys- (SEQ ID NO: 23), NH$_2$-Ala-Cys-Asn-Leu-Ser-Ala-Cys- (SEQ ID NO: 24), Cys-Ser-Asn-Thr-Ala-Ala-Cys- (SEQ ID NO: 25), NH$_2$-Ala-Cys-Asp-Thr-Ala-Leu-Cys- (SEQ ID NO: 26), NH$_2$-Ala-Cys-Asp-Thr-Ala-Ile-Cys- (SEQ ID NO: 27), NH$_2$-Ala-Cys-Asp-Thr-Ala-Leu-Cys- (SEQ ID NO: 28), NH$_2$-Ala-Cys-Asp-Thr-Ala-ile-Cys- (SEQ ID NO: 29), NH$_2$-Ala-Cys-Asp-Leu-Ser-Val-Cys- (SEQ ID NO: 30), NH$_2$-Ala-Cys-Asp-Leu-Ser-Val-Cys- (SEQ ID NO: 31), NH$_2$-Ala-Cys-Asn-Leu-Ser-Val-Cys (SEQ ID NO: 32), and NH$_2$-Cys-Ser-Asn-Thr-Ala-Val-Cys- (SEQ ID NO: 33); $Y^1$ can be -Val-Leu-Gly-Arg-Leu-Ser-Gln-Glu-Leu-His-Arg-Leu-Gln-Thr-Tyr-Pro-Arg-Thr-Asn- (SEQ ID NO: 34) or -Val-Leu-Gly-Lys-Leu-Ser-Gln-Glu-Leu-His-Lys-Leu-Gln-Thr-Tyr-Pro-Arg-Thr-Asn- (SEQ ID NO: 35); and $Z^1$ can be -Val-Gly-Ser-Lys-Ala-Phe having a carboxy-terminus (SEQ ID NO: 46) or -Val-Gly-Ser-Lys-Ala-Phe-NH$_2$ (SEQ ID NO: 47).

In some embodiments of the modified calcitonin gene-related peptide antagonist having the structure of Formula I, the antagonist comprises from 28 to 35 amino acid residues, from 31 to 37 amino acid residues, from 31 to 33 amino acid residues or 32 amino acid residues.

In some embodiments of the modified calcitonin gene-related peptide antagonist having the structure of Formula I, the antagonist comprises -Ala-Cys-Asp-Thr-Ala-$X^{16}$-Cys- (SEQ ID NO: 49) motif, wherein $X^{16}$ is any amino acid residue other than Thr.

In some embodiments of the modified calcitonin gene-related peptide antagonist having the structure of Formula I, the antagonist comprises a first peptide fragment having seven amino acid residues or less, wherein said first peptide fragment has a sequence from modified calcitonin gene-related peptide. In some embodiments of the modified calcitonin gene-related peptide antagonist having the structure of Formula I, the antagonist comprises a second peptide fragment having seven amino acid residues or less, wherein said first and second peptide fragments are non-contiguous and each independently have a sequence which may be modified from calcitonin gene-related peptide. In some embodiments of the modified calcitonin gene-related peptide antagonist having the structure of Formula I, the antagonist comprises a third peptide fragment having 20 amino acid residues or less, wherein said third peptide fragment has a sequence from salmon calcitonin. In some embodiments of the modified calcitonin gene-related peptide antagonist having the structure of Formula I, the second peptide fragment and the third peptide fragment are contiguous.

In some embodiments, the antagonist has a structure selected from the list of structures consisting of NH$_2$-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 1), NH$_2$-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 2), NH$_2$-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 3), NH$_2$-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 4), NH$_2$-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID. NO: 5), NH$_2$-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 6), NH$_2$-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 7), NH$_2$-Cys-S er-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 8), NH$_2$-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 9), NH$_2$-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 10), NH$_2$-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 11), NH$_2$-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NFI$_2$ (SEQ ID NO: 12), or NH$_2$-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH$_2$ (SEQ ID NO: 13), Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH$_2$ (SEQ ID NO: 14), or Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH$_2$ (SEQ ID NO: 15) or a pharmaceutically acceptable salt thereof. The instant antagonist can be a single compound from the above list.

In some embodiments, the antagonist has a structure of NH$_2$-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 1), or a pharmaceutical acceptable salt thereof. In some embodiments, the antagonist has a structure of NH$_2$-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 2), or a pharmaceutical acceptable salt thereof. In some embodiments, the antagonist has a structure of NH$_2$-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 3), or a pharmaceutical acceptable salt thereof. In some embodiments, the antagonist has a structure of NH$_2$-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 4), or a pharmaceutical acceptable salt thereof. In some embodiments, the antagonist has a structure of NH$_2$-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 5), or a pharmaceutical acceptable salt thereof. In some embodiments, the antagonist has a structure of NH$_2$-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 6), or a pharmaceutical acceptable salt thereof. In some embodiments, the antagonist has a structure of NH$_2$-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 7), or a pharmaceutical acceptable salt thereof. In some embodiments, the antagonist has a structure of NH$_2$-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 8), or a pharmaceutical acceptable' salt thereof. In some embodiments, the antagonist has a structure of NH$_2$-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 9), or a pharmaceutical acceptable salt thereof. In some embodiments, the antagonist has a structure of NH$_2$-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 10), or a pharmaceutical acceptable salt thereof. In some embodiments, the antagonist has a structure of NH$_2$-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ. ID NO: 11), or a pharmaceutical acceptable salt thereof. In some embodiments, the antagonist has a structure of NH$_2$-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 12), or a pharmaceutical acceptable salt thereof. In some embodiments, the antagonist has a structure of or NH$_2$-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH$_2$ (SEQ ID NO: 13), or a pharmaceutical acceptable salt thereof. In some embodiments, the antagonist has a structure of Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH$_2$ (SEQ ID NO: 14), or a pharmaceutical acceptable salt thereof. In some embodiments, the antagonist has a structure of or Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH$_2$ (SEQ ID NO: 15), or a pharmaceutical acceptable salt thereof. The antagonist of the present disclosure can also be pharmaceutical composition comprising one of the compounds above. The pharmaceutical composition can be used in a method for treating a headache in an individual, the method comprising administering to an individual an effective amount of a modified calcitonin gene-related peptide antagonist.

In some embodiments of the modified calcitonin gene-related peptide antagonist having the structure of Formula I, Y$^1$ includes -Ala-Glu-Ala-Ala-Ala-Lys-Glu-Ala-Ala-Ala-Lys-Glu-Ala-Ala-Ala-Lys-Ala- (SEQ ID NO: 50), -Ala-Lys-Ala-Ala-Ala-Glu-Lys-Ala-Ala-Ala-Glu-Lys-Ala-Ala-Ala-Glu-Ala- (SEQ ID NO: 51), -Ala-Glu-Ala-Ala-Lys-Ala-Glu-Ala-Ala-Lys-Ala-Glu-Ala-Ala-Lys-Ala- (SEQ ID NO: 52), or -Ala-Lys-Ala-Ala-Glu-Ala-Lys-Ala-Ala-Glu-Ala-Lys-Ala-Ala-Glu-Ala- (SEQ ID NO: 53).

Some embodiments provide a modified calcitonin gene-related peptide antagonist having the structure of a peptide sequence of Table 1.

Some embodiments provide a modified calcitonin gene-related peptide antagonist, comprising an amino acid sequence having at least 80% sequence identity to the amino acid sequence of SEQ ID NOS: 1, 2, 3, 4, 5, 6, 7, 8, 9, 10, 11, 12, 13, 14 or 15 wherein said peptide retains antagonist activity. In some embodiments, the amino acid sequence can have at least 90% sequence identity to the amino acid sequence of SEQ ID NOS: 1, 2, 3, 4, 5, 6, 7, 8, 9, 10, 11, 12, 13, 14 or 15 wherein said peptide retains antagonist activity. In some embodiments, the amino acid sequence can have at least 95% sequence identity to the amino acid sequence of SEQ ID NOS: 1, 2, 3, 4, 5, 6, 7, 8, 9, 10, 11, 12, 13, 14 or 15 wherein said peptide retains antagonist activity. In some embodiments, the amino acid sequence can have at least 97% sequence identity to the amino acid sequence of SEQ ID NOS: 1, 2, 3, 4, 5, 6, 7, 8, 9, 10, 11, 12, 13, 14 or 15 wherein said peptide retains antagonist activity.

Some embodiments provide a pharmaceutical composition comprising a pharmaceutically acceptable excipient and the instant modified calcitonin gene-related peptide antagonist as disclosed and described herein.

Some embodiments provide a method of treating a headache in an individual, the method comprising administering to the individual an effective amount of the instant modified calcitonin gene-related peptide antagonist as disclosed and described herein. In some embodiments, the method can further comprise identifying a subject suffering from headache. In some embodiments, the headache is a migraine.

Some embodiments provide a method of treating a condition associated with aberrant levels of CGRP comprising the administration of the instant modified calcitonin gene-related peptide antagonist as disclosed and described herein, to an individual, the method comprising administering to the individual an effective amount of a modified calcitonin gene-related peptide antagonist as disclosed and described herein. In some embodiments, the condition is a migraine.

Some embodiments provide a conjugate which comprises a therapeutic agent linked to the instant modified calcitonin gene-related peptide antagonist as disclosed and described herein that selectively binds to a member of the CGRP receptor family. In some embodiments, the therapeutic agent can be an imaging agent.

Some embodiments provide a method of identifying a CGRP receptor binding ligand by providing the instant modified calcitonin gene-related peptide antagonist bound to a CGRP receptor, providing a test compound or library of test compounds, and identifying compounds which are capable of dissociating the modified calcitonin gene-related peptide antagonist from the CGRP receptor. Such compounds identified by this method may be further screened against other CGRP receptors and CGRP receptor binding agents to identify selective CGRP receptor binding ligands.

In some embodiments herein a modified CGRP antagonist is described that retains the sequence of an agonist that include $X^1$, the N-terminal region that binds the CGRP receptor at the cellular membrane, and at its C-terminal, initiates and stabilizes the helix through a disulfide bond $Y^1$, the helix structural motif; and $Z^1$, the C-terminal binding region, but that differs by as little as one residue from the agonist sequence. In a preferred embodiment, the salmon calcitonin derived helix is part of the structure used to increase efficacy of the instant antagonist.

Definitions

The following definitions are set forth to illustrate and define the meaning and scope of the various terms used to describe the embodiments.

As used herein, "modified" refers to a polypeptide which retains the overall structure of a related polypeptide but which differs by at least one residue from that related polypeptide. As used herein a "modified C-terminus" is a C-terminus of a polypeptide that has a chemical structure other than a standard peptide carboxy group, an example of such a modified C-terminus being a C-terminal carboxamide.

As used herein, "agonist" refers to a biologically active ligand which binds to its complementary biologically active receptor and activates the latter either to cause a biological response in the receptor or to enhance preexisting biological activity of the receptor.

As used herein, "antagonist" refers to a biologically active ligand which binds to its complementary biologically active receptor and inhibits the physiological response of the receptor.

As used herein, "pharmaceutically acceptable salt" refers to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the modified calcitonin gene-related peptide antagonists disclosed herein with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like. Thus, the term refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluene-sulfonic acid, salicylic acid and the like. For a description of pharmaceutically acceptable salts as prodrugs, see Bundgaard, H. ed., 1985 *Design of Prodrugs*, Elsevier Science Publishers, Amsterdam.

As used herein, "pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H. ed. 1985 *Design of Prodrugs*, Elsevier Science Publishers, Amsterdam. These esters are typically formed from the corresponding carboxylic acid and an alcohol. Generally, ester formation can be accomplished via conventional synthetic techniques. See, for example, March, 1992 *Advanced Organic Chemistry*, 4th Ed., John Wiley & Sons, New York, p.p. 393-396 and references cited therein, and Mark, et al. 1980 *Encyclopedia of Chemical Technology*, John Wiley & Sons, New York. The alcohol component of the ester will generally comprise (i) a $C_2$-$C_{12}$ aliphatic alcohol that can or cannot contain one or more double bonds and can or cannot contain branched carbons or (ii) a $C_7$-$C_{12}$ aromatic or heteroaromatic alcohols.

As used herein, "C-terminal amide" refers to an amide moiety which replaces the C-terminal hydroxyl moiety usually present at the carboxy-terminus of a polypeptide, such that the polypeptide ends with a carboxamide (i.e., C(=O)—NH2 rather than a C-terminal carboxy (i.e. C(=O)—OH) moiety. For a description of pharmaceutically acceptable amides as prodrugs, see Bundgaard, H. ed. 1985 *Design of Prodrugs* Elsevier Science Publishers, Amsterdam. These amides are typically formed from the corresponding carboxylic acid and an amine. Generally, amide formation can be accomplished via conventional synthetic techniques. See, for example, March, 1992 *Advanced Organic Chemistry*, 4th Ed., John Wiley & Sons, New York, p. 393 and Mark, et al. 1980 *Encyclopedia of Chemical Technology*, John Wiley & Sons, New York.

As used herein, "pharmaceutically acceptable carrier" refers to a carrier medium which does not interfere with the effectiveness of the biological activity of the active ingredients and which is not toxic to the host or patient.

As used herein, "stereoisomer" refers to an entity having the same molecular weight, chemical composition, and bonding sequence as another, but having its atoms grouped differently in space about one or more chiral centers. That is, stereoisomers of the same chemical formula will contain identical chemical moieties located in different spatial orientations about at least one chiral center. When pure, stereoisomers have the ability to rotate plane-polarized light. Some pure stereoisomers, however, may have an optical rotation that is so slight that it is undetectable with present instrumentation. The modified calcitonin gene-related peptide antagonists as disclosed herein may have one or more asymmetrical carbon atoms and therefore include various stereoisomers. All stereoisomers are included within the scope of the embodiments.

As used herein, "therapeutically" or "pharmaceutically-effective amount" as applied to the compositions as disclosed herein refers to the amount of composition sufficient to induce a desired biological result. That result can be alleviation of the signs, symptoms, or causes of a disease, or any other desired alteration of a biological system.

As used herein, the terms "peptide residue" and "peptidic structure" are intended to include peptides comprised of naturally-occurring L-amino acids and the corresponding D-amino acids, as well as peptide derivatives, peptide analogues and peptidomimetics of the naturally-occurring L-amino acid, structures. Approaches to designing peptide analogues, derivatives and mimetics are known in the art. For example, see Farmer, P. S. in: *Drug Design* E. J. Ariens, ed. Academic Press, New York, 1980, vol. 10, pp. 119-143; Ball J. B. & Alewood, P. F. 1990 *J. Mol. Recognition* 3:55; Morgan, B. A. & Gainor, J. A. 1989 *Ann. Rep. Med. Chem.* 24:243; and Freidinger, R. M. 1989 *Trends Pharmacol. Sci.* 10:270; Luthman, et al. 1996 *A Textbook of Drug Design and Development*, 14:386-406, 2nd Ed., Harwood Academic Publishers; Joachim Grante, Angew. 1994 *Chem. Int. Ed. Engl.* 33:1699-1720; Fauchere, J. 1986 *Adv. Drug Res.* 15:29; Veber and Freidinger 1985 *TINS* p. 392; Evans, et al. 1987 *J. Med. Chem.* 30:229, all of which are hereby incorporated by reference in their entireties. Peptidomimetics that are structurally similar to therapeutically useful peptides may be used to produce an equivalent or enhanced therapeutic or prophylactic effect, by methods known in the art and further described in the following references: Spatola, A. F. 1983 in: *Chemistry and Biochemistry of Amino Acids, Peptides, and Proteins*, B. Weinstein, eds., Marcel Dekker, New York, p. 267; Spatola, A. F. 1983 *Vega Data*, Vol. 1, Issue 3, *Peptide Backbone Modifications* (general review); Morley, 1980 *Trends. Pharm. Sci.* pp. 463-468, (general review); Hudson, et al. 1979 *Int. J. Pept. Prot. Res.* 14:177-185 (—$CH_2NH$—, $CH_2CH_2$—); Spatola, et al. 1986 *Life Sci.* 38:1243-1249 (—$CH_2$—S); Hann, 1982 *J. Chem. Soc. Perkin. Trans. I* 307-314 (—CH—CH—, cis and trans); Almquist, et al. 1980 *J. Med. Chem.* 23:1392-1398, (—$COCH_2$—); Jennings-White, et al. 1982 *Tetrahedron Lett.* 23:2533 (—$COCH_2$—); Szelke, et al. 1982 European Appln. EP 45665 (—$CH(OH)CH_2$—); Holladay, et al. 1983 *Tetrahedron Lett.* 24:4401-4404 (—$C(OH)CH_2$—); and Hruby, 1982 *Life Sci.* 31:189-199 (—$CH_2$—S—); each of which is incorporated herein by reference in its entirety.

Systematic substitution of one or more amino acids of a consensus sequence with a D-amino acid of the same type (for example, D-lysine in place of L-lysine) may be used to generate more stable peptides. In addition, constrained peptides comprising a consensus sequence or a substantially identical consensus sequence variation may be generated by methods known in the art (Rizo, et al. 1992 *Ann. Rev. Biochem.* 61:387, incorporated herein by reference in their entireties); for example, by adding internal cysteine residues capable of forming intramolecular disulfide bridges which cyclize the peptide or the use of aminoisobutyric acid (Aib) residues to stabilize the helix.

Synthetic or non-naturally occurring amino acids refer to amino acids which do not naturally occur in vivo but which, nevertheless, can be incorporated into the peptide structures described herein.

As used herein, a "derivative" of a compound, for example, a peptide or amino acid, refers to a form of that compound in which one or more reactive groups in the compound have been derivatized with a substituent group. Examples of peptide derivatives include peptides in which an amino acid side chain, the peptide backbone, or the amino- or carboxy-terminus has been derivatized (for example, peptidic compounds with methylated amide linkages or hydroxylated amino acids or amino acid residues).

As used herein an "analogue" of a compound refers to a compound which retains chemical structures of the reference compound necessary for functional activity of that compound yet which also contains certain chemical structures which differ from the reference compound. An example of an analogue of a naturally occurring peptide is a peptide which includes one or more non-naturally-occurring amino acids or conservative amino acid substitutions, such as, for example, a substitution indicated in Table 3, below. As used herein, a "mimetic" of a compound refers to a compound in which chemical structures of the referenced compound necessary for functional activity of that compound have been replaced with other chemical structures which mimic the conformation of the referenced compound. Examples of peptidomimetics include peptidic compounds in which the peptide backbone is substituted with one or more benzodiazepine molecules (see for example, James, G. L. et al. 1993 *Science* 260:1937-1942 which is hereby incorporated by reference in its entirety), peptides in which all L-amino acids are substituted with the corresponding D-amino acids and "retro-inverso" peptides (see U.S. Pat. No. 4,522,752 by Sisto, which is hereby incorporated by reference in its entirety), described further below, James, G. L. et al. 1993 *Science* 260:1937-1942, and Goodman et al. 1981 *Perspectives in Peptide Chemistry* pp. 283-294 which is hereby incorporated by reference in its entirety. See also U.S. Pat. No. 4,522,752 by Sisto, which is hereby incorporated by reference in its entirety, for further description of "retro-inverso" peptides. Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

As used herein, the term "amino acid structure" (such as a "leucine structure", a "phenylalanine structure" or a "glutamine structure") is intended to include the amino acid, as well as analogues, derivatives and mimetics of the amino acid that maintain the functional activity of the compound. For example, the term "phenylalanine structure" is intended to include phenylalanine as well as pyridylalanine and homophenylalanine. The term "leucine structure" is intended to include leucine, as well as substitution with valine, isoleucine or other natural or non-natural amino acid having an aliphatic side chain, such as norleucine.

The amino- and/or carboxy-terminus of the modified peptide compounds disclosed herein can be standard amino and carboxy termini as seen in most proteins. Alternatively, the amino- and/or carboxy-terminus of the peptide compound can be chemically altered by the addition or replacement of a derivative group. Amino-derivative groups which can be present at the N-terminus of a peptide compound (i.e., can be Y1) include acetyl, aryl, aralkyl, acyl, epoxysuccinyl and cholesteryl groups. Carboxy-derivative groups which can be present at the C-terminus of a peptide compound (i.e., can be Y2) include alcohol, aldehyde, epoxysuccinate, acid halide, carbonyl, halomethane, diazomethane groups and carboxamide. Carboxamide is preferred.

As used herein, "detectable label" or "imaging agent" refers to materials, which when covalently attached to a compound, permit detection of the compound, including but not limited to, detection in vivo in a patient to whom a modified calcitonin gene-related peptide antagonist has been administered. Suitable detectable labels are well known in the art and include, by way of example, radioisotopes, fluorescent labels (for example, fluorescein), and the like. The particular detectable label employed is not critical and is selected relative to the amount of label to be employed as well as the toxicity of the label at the amount of label employed. Selection of the label relative to such factors is well within the skill of the art.

Covalent attachment of the detectable label to the peptide or peptidomimetic is accomplished by conventional methods well known in the art. For example, when the $^{125}$I radioisotope is employed as the detectable label, covalent attachment of $^{125}$I to the peptide or the peptidomimetic can be achieved by incorporating the amino acid tyrosine into the peptide or peptidomimetic and then iodinating the peptide (see, for example, Weaner, et al. 1994 *Synthesis and Applications of Isotopically Labelled Compounds*; pp. 137-140). If tyrosine is not present in the peptide or peptidomimetic, incorporation of tyrosine to the N or C terminus of the peptide or peptidomimetic can be achieved by well-known chemistry. Likewise, $^{32}$P can be incorporated onto the peptide or peptidomimetic as a phosphate moiety through, for example, a hydroxyl group on the peptide or peptidomimetic using conventional chemistry.

As used herein the term "therapeutic agent" means an agent capable of having a desired therapeutic effect for a specific disease indication, including without limitation, a migraine or pain reducing agent.

As used herein, the term "α-helix" means a structural component that forms an α-helical protein structure or any other structural analogue which results in a similar positioning of the $X_1$ and $Z^1$ domains on a receptor.

Preparation of Peptides and Peptidomimetics

1. Solid Phase Synthesis

The modified calcitonin gene-related peptide antagonists described herein can be prepared by classical methods known in the art, for example, by using standard solid phase techniques. See, for example, Merrifield, 1963 *J. Am. Chem. Soc.* 85:2149, incorporated herein by reference in their entirety.

These solid phase peptide synthesis procedures are well known in the art and further described by J. M. Stewart and J. D. Young, 1984 *Solid Phase Peptide Syntheses* 2nd Ed., Pierce Chemical Company.

2. Synthetic Amino Acids

These procedures can also be used to synthesize peptides in which amino acids other than the 20 naturally occurring, genetically encoded amino acids are substituted at one, two, or more positions of any of the modified calcitonin gene-related peptide antagonists as disclosed herein. For instance, naphthylalanine can be substituted for tryptophan, facilitating synthesis. Other synthetic amino acids that can be substituted into the peptides of the present embodiments include L-hydroxypropyl, L-3,4-dihydroxy-phenylalanyl, d amino acids such as L-d-hydroxylysyl and D-d-methylalanyl, L-α-methylalanyl, β-amino acids, and isoquinolyl. D amino acids and non-naturally occurring synthetic amino acids can also be incorporated into the peptides of the present embodiments (see, for example, Roberts, et al. 1983 *Unusual Amino/Acids in Peptide Synthesis* 5:341-449).

In some embodiments, the naturally occurring side chains of the 20 genetically encoded amino acids, or any other side chain as disclosed herein can be transposed to the nitrogen of the amino acid, instead of the α-carbon as typically found in peptides.

Table 2: One-letter abbreviations for the canonical amino acids. Three-letter abbreviations are in parentheses.

TABLE 2

| | |
|---|---|
| Alanine (Ala) | A |
| Glutamine (Gln) | Q |
| Leucine (Leu) | L |
| Serine (Ser) | S |
| Arginine (Arg) | R |
| Glutamic Acid (Glu) | E |

TABLE 2-continued

| | |
|---|---|
| Lysine (Lys) | K |
| Threonine (Thr) | T |
| Asparagine (Asn) | N |
| Glycine (Gly) | G |
| Methionine (Met) | M |
| Tryptophan (Trp) | W |
| Aspartic Acid (Asp) | D |
| Histidine (His) | H |
| Phenylalanine (Phe) | F |
| Tyrosine (Tyr) | Y |
| Cysteine (Cys) | C |
| Isoleucine (Ile) | I |
| Proline (Pro) | P |
| Valine (Val) | V |

Nomenclature and Symbolism for Amino Acids and Peptides by the UPAC-IUB Joint Commission on Biochemical Nomenclature (JCBN) have been published in the following documents: *Biochem. J.*, 1984, 219, 345-373; *Eur. J. Biochem.*, 1984, 138, 9-5 37; 1985, 152, I; 1993, 213, 2; *Internat. J. Pept. Prot. Res.*, 1984, 24, following p 84; *J. Biol. Chem.*, 1985, 260, 14-42; *Pure Appl. Chem.*, 1984, 56, 595-624; *Amino Acids and Peptides*, 1985, 16, 387-410; *Biochemical Nomenclature and Related Documents*, 2$^{nd}$ edition, Portland Press, 1992, pages 39-69.

In some embodiments, the amino acid sequence of the instant modified calcitonin gene-related peptide antagonist can be modified, relative to the sequence of SEQ ID NOS: 1, 2, 3, 4, 5, 6, 7, 8, 9, 10, 11, 12, 13, 14 or 15 such that the modification reduces the instant modified calcitonin gene-related peptide antagonist's susceptibility to enzymatic proteolysis. In some embodiments this modification may comprise the N-terminal addition of a sequence comprising all or part of the 864 residue XTENS polypeptide, a polypeptide that has been shown to increase protein stability after administration to a subject See, for example, Schellenberger, et al., 2009, *Nature Biotechnology* 27(12): 1186-1192, which is hereby incorporated by reference in its entirety.

In some embodiments, the instant modified calcitonin gene-related peptide antagonist can include one or more D-amino acids residues. In some embodiments, the amino acid sequence of the instant modified calcitonin gene-related peptide antagonist can be modified, relative to the sequence of SEQ ID NOS: 1, 2, 3, 4, 5, 6, 7, 8, 9, 10, 11, 12, 13, 14 or 15 such that the modification includes replacement of one or more L-amino acids residues with corresponding D-amino acids residues.

In some embodiments, the amino acid sequence of the modified calcitonin gene-related peptide antagonist can be modified, relative to the sequence of SEQ ID NOS: 1, 2, 3, 4, 5, 6, 7, 8, 9, 10, 11, 12, 13, 14 or 15 such that the modification includes substitution with a conservative amino acid.

Naturally occurring residues may be divided into classes based on common side chain properties:
  hydrophobic: norleucine (Nor), Met, Ala, Val, Leu, De;
  neutral hydrophilic: Cys, Ser, Thr, Asn, Gln;
  acidic: Asp, Glu;
  basic: His, Lys, Arg;
  residues that influence chain orientation: Gly, Pro; and
  aromatic: Trp, Tyr, Phe.

Conservative amino acid substitutions may involve exchange of a member of a class with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acids.

In some embodiments, conservative substitutions can include the substitution of one non-polar (hydrophobic) amino acid residue such as isoleucine, valine, leucine norleucine, alanine, or methionine for another, the substitution of one polar (hydrophilic) amino acid residue for another such as between arginine and lysine, between glutamine and asparagine, between threonine and serine, the substitution of one basic amino acid residue such as lysine, arginine or histidine for another, or the substitution of one acidic residue, such as aspartic acid or glutamic acid for another. The phrase "conservative amino acid substitution" also includes the use of a chemically derivatized residue in place of a non-derivatized residue, provided that such polypeptide displays the requisite antagonist activity.

Table 3 provides examples of amino acid residue substitutions that can be useful in accordance with the present embodiments.

TABLE 3

| Original Residues | Substitutions |
|---|---|
| Ala | Val, Leu, Ile, Aib |
| Arg | Lys, Gln, Asn, homoarginine |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4-Diamino-butyric Acid, Gln, Asn, ornithine |
| Met | Leu, Phe, Ile |
| Phe | Leu, Val, Ile, Ala, Tyr |
| Pro | Ala |
| Ser | Thr, Ala, Cys |
| Thr | Ser, Val, Ile |
| Trp | Tyr, Phe |
| Tyr | Trp, Phe, Thr, Ser |
| Val | Ile, Met, Leu, Phe, Ala, Norleucine |

In some embodiments, a basic moiety of an amino acid as disclosed herein, such as the guanidine of Arg, can be replaced by a base bioisostere.

"hydroxyproline" refers to any and all known hydroxylation relatives of proline either as a free amino acid or incorporated into a polypeptide. It includes (2S,4R)-4-hydroxyproline, as well as proline residues with differing stereochemistries or hydroxylated carbons.

An "O-carboxy" group refers to an "RC(=O)O-" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

A "C-carboxy" group refers to a "—C(=O)OR" group in which R can be the same as defined with respect to O-carboxy. A C-carboxy may be substituted or unsubstituted.

A "C-amido" group refers to a "—C(=O)NR$^A$R$^B$" group in which R$^A$ and R$^B$ may or may not be the same and can be defined as R is defined with respect to O-carboxy. A C-amido may be substituted or unsubstituted.

An "N-amido" group refers to an "RC(=O)NR$^A$-" group in which R and R$^A$ may or may not be the same and can be defined as R is defined with respect to O-carboxy. An N-amido may be substituted or unsubstituted.

As used herein, an "amide" refers to a "—C(=O)NR$^A$—" group in which R$^A$ and R$^B$ may or may not be the same and can be defined as R is defined with respect to O-carboxy. R$^A$ and RB may be Hydrogen in some embodiments.

As used herein, an "amine" refers to a "—NR$^A$R$^B$" group in which R$^A$ and R$^B$ may or may not be the same and can be defined as R is defined with respect to O-carboxy.

As used herein, an "urea" refers to —NR$^A$C(=O)NR$^B$$_2$ where each R$^A$ and R$^B$ is individually defined as R is defined with respect to O-carboxy.

One can also readily modify the peptides of the instant embodiments by phosphorylation (see, for example, W. Bannwarth, et al. 1996 *Biorganic and Medicinal Chemistry Letters* 6:2141-2146), and other methods for making peptide derivatives of the compounds of the present embodiments are described in Hruby, et al. 1990 *Biochem. J.* 268:249-262. Thus, the peptides as disclosed herein also serve as a basis to prepare peptidomimetics with similar biological activity.

3. Terminal Modifications

Those of skill in the art recognize that a variety of techniques are available for constructing peptidomimetics with the same or similar desired biological activity as the corresponding modified calcitonin gene-related peptide antagonist but with more favorable activity than the reference peptide with respect to solubility, stability, and susceptibility to hydrolysis and proteolysis. See, for example, Morgan, et al. 1989 *Ann. Rep. Med. Chem.* 24:243-252. The following describes methods for preparing peptidomimetics modified at the N-terminal amino group, the C-terminal carboxyl group, and/or changing one or more of the amido linkages in the peptide to a non-amido linkage. It being understood that two or more such modifications can be coupled in one peptidomimetic structure (for example, modification at the C-terminal carboxyl group and inclusion of a —CH$_2$-carbamate linkage between two amino acids in the peptide).

1). N-Terminal Modifications

Peptides typically are synthesized as the free acid but, as noted above, could be readily prepared as the amide or ester. One can also modify the amino and/or carboxy terminus of the peptide compounds to produce other useful compounds. Amino terminus modifications include methylation (i.e., —NHCH$_3$ or —NH(CH$_3$)$_2$), acetylation, adding a benzyloxycarbonyl group, or blocking the amino terminus with any blocking group containing a carboxylate functionality defined by RCOO—, where R is selected from the group consisting of naphthyl, acridinyl, steroidyl, and similar groups.

Amino terminus modifications are as recited above and include alkylating, acetylating, adding a carbobenzoyl group, forming a succinimide group, etc. (See, for example, Murray, et al. 1995 *Burger's Medicinal Chemistry and Drug Discovery* 5th ed., Vol. 1, Manfred E. Wolf, ed., John Wiley and Sons, Inc., which is hereby incorporated by reference in its entirety).

The N-terminus may also be modified through the addition of at least one residues N-terminal to the X$^1$ fragment. Techniques for assessing the impact of N-terminal extensions to peptides are known in the art in, for example, Schellenberger, et al., 2009, *Nature Biotechnology* 27(12): 1186-1192, which is herein incorporated by reference in their entirety.

2). C-Terminal Modifications

Carboxy terminus modifications include replacing the free acid with a carboxamide group or forming a cyclic lactam at the carboxy terminus to introduce structural constraints. In preparing peptidomimetics wherein the C-terminal carboxyl group is replaced by the amide —C(O)NR$^3$R$^4$, a benzhydrylamine resin is used as the solid support for peptide synthesis.

Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR$^1$ where R and R$^1$ are as defined above). Side chain protection is then removed in the usual fashion by treatment with hydrogen fluoride to give the free amides, alkylamides, or dialkylamides.

In addition to the foregoing N-terminal modifications, the modified peptide antagonists described herein, including peptidomimetics, can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. Quite surprisingly, the foregoing can be accomplished with little, if any, diminishment in their binding activity. In some embodiments, the modified calcitonin gene-related peptide antagonists as disclosed and described herein can be derivatized with or coupled to such polymers using any of the methods set forth in Zallipsky, S. 1995 *Bioconjugate Chem* 6:150-165; Monfardini, C, et al. 1995 *Bioconjugate Chem* 6:62-69; U.S. Pat. Nos. 4,640,835; 4,496,689; 4,301,144; 4,670,417; 4,791,192; 4,179,337 or WO 95/34326, all of which are incorporated by reference in their entirety.

4. Backbone Modifications

Other methods for making peptide derivatives of the compounds are described in Hruby, et al. 1990 *Biochem. J.* 268 (2):249-262, incorporated herein by reference in its entirety. Thus, the peptide compounds also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan, et al. 1989 *Ann. Rep. Med. Chem.* 24:243-252, incorporated herein by reference in its entirety.

5. Disulfide Bond Formation

The compounds may exist in a cyclized form with an intramolecular disulfide bond between the thiol groups of the cysteines.

Other embodiments include analogs of these disulfide derivatives in which one of the sulfurs has been replaced by a CH$_2$ group or other isostere for sulfur. These analogs can be made via an intramolecular or intermolecular displacement, using methods known in the art.

Alternatively, the amino-terminus of the peptide can be capped with an alpha-substituted acetic acid, wherein the alpha substituent is a leaving group, such as an α-haloacetic acid, for example, α-chloroacetic acid, α-bromoacetic acid, or α-iodoacetic acid. The peptides of the present embodiments can be cyclized or dimerized via displacement of the leaving group by the sulfur of the cysteine or homocysteine residue. See, for example, Andreu, et al. 1994, *Meth. Mol. Bio.* 35(7):91-169; Barker, et al. 1992, *J. Med. Chem.* 35:2040-2048; and Or, et al. 1991, *J. Org. Chem.* 56:3146-3149, each of which is incorporated herein by reference in its entirety.

In some embodiments, the modified calcitonin gene-related peptide antagonists as disclosed and described herein may also be prepared by recombinant DNA techniques well known in the art.

Some embodiments include pharmaceutical compositions comprising, as an active ingredient, at least one of the instant modified peptides, or peptidomimetics disclosed herein in association with a pharmaceutical carrier or diluent. These pharmaceutical compositions can be administered by any means, as known to those of skill in the art, and include, without limitation, oral, pulmonary, parenteral (intramuscular, intraperitoneal, intravenous, or subcutaneous injection), inhalational (via a fine powder formulation, or aerosol), transdermal, intranasal or sublingual routes of administration and can be formulated in dosage forms appropriate for each route of administration. See, for example, Bernstein, et al. PCT Patent Publication No. WO 93/25221, published Dec. 23, 1993; Pitt, et al. PCT Patent Publication No. WO 94/17784, published Aug. 18, 1994; and Pitt, et al. European Patent Application 613,683, published Sep. 7, 1994, each of which is incorporated herein by reference in its entirety. The compounds can also be administered in sustained or controlled release dosage forms, including without limitation, depot injections, osmotic pumps, transdermal (including electrotransport) patches, and the like, for prolonged and/or timed, pulsed administration at a predetermined rate.

The pharmaceutical compositions of the present embodiments may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present embodiments thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the instant compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the instant compounds can be formulated by combining the active compounds with pharmaceutically acceptable carriers, such as those disclosed in D. J. Sarubbi, Oral GLP-1 Formulations, US Patent App. No. 2010/0016229 A1, published Jan. 21, 2010, which is herein incorporated by reference in its entirety. As discussed therein, oral administrations can take the form of tablets or capsules of pharmaceutically acceptable carriers mixed with the drug. Additional suitable delivery agents taught in Goldberg, 2009, Compositions for Delivering Parathyroid Hormone and Calcitonin, US Patent App. No. 2009/0264368 A1, published Oct. 22, 2009 (which is herein incorporated by reference in its entirety) include any known liquid or solid dosage form.

For administration by inhalation, the instant compounds for use according to the present embodiments are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. As an example, preparations for administration by inhalation may be prepared according to the teaching of Quay, et al., U.S. Pat. No. 7,812,120 B2, issued Oct. 12, 2010, which is herein incorporated by reference in its entirety.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eye drops, or in gellan gum (Shedden et al., 2001, *Clin. Ther.,* 23(3):440-50) or hydrogels (Mayer et al., 1996, *Ophthalmologica,* 210(2):101-3); ophthalmic ointments; ophthalmic suspensions, such as microparticulates, drug-containing small polymeric particles that are suspended in a liquid carrier medium (Joshi, A., *J. Ocul. Pharmacol.,* 1994 10(1):29-45), lipid-soluble formulations (Alm et al., 1989 *Prog. Clin. Biol. Res.,* 312:447-58), and microspheres (Mordenti, 1999, *Toxicol. Sci.,* 52(1):101-6); and ocular inserts. All of the above-mentioned references are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in, many respects nasal secretions to ensure maintenance of normal ciliary action, such compositions include, for example and without limitation, the nasal solutions disclosed by Azria, et al., in U.S. Pat. No. 5,733,569, issued Mar. 31, 1998 which is incorporated herein, by reference, in its entirety. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

In addition to the formulations described previously, the instant compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Depending on the chemical nature and the biological stability of the therapeutic reagent, additional strategies for peptide stabilization may be employed.

Additional therapeutic or diagnostic agents may be incorporated into the pharmaceutical compositions. Alternatively or additionally, pharmaceutical compositions may be combined with other compositions that contain other therapeutic or diagnostic agents.

Non-limiting examples of methods of administration include, among others, (a) administration though oral pathways, such as those described in M. Goldberg, Publication No. US 2009/0264368 A1, published Oct. 22, 2009 which is herein incorporated by reference in its entirety, and in D. Sarubbi, Publication No. US 2010/0016229 A1, published Jan. 21, 2010, which is herein incorporated by reference in its entirety; (b) administration may also be through non-oral pathways such as intraocular, intranasal or intraauricular, which administration includes administration as an aqueous suspension, an oily preparation or the like or as a drip, spray, salve, ointment or the like; (c) administration via injection, subcutaneously, intraperitoneally, intravenously, intramuscularly, intradermally, intraorbitally or the like, including infusion pump delivery; (d) administration locally such as by injection directly intracranially, e.g., by depot implantation; as well as (e) administration topically; as deemed appropriate by those of skill in the art for bringing the peptide of the present embodiments into contact with living tissue. A non-limiting representative example of nasal application is described in Quay, et al., U.S. Pat. No. 7,812,120 B2, issued Oct. 12, 2010, which is herein incorporated by reference in its entirety.

The exact formulation, route of administration and dosage for the pharmaceutical compositions of the present embodiments can be chosen by the individual physician in view of the patient's condition. (See e.g., Fingl et al. 1975, in "The Pharmacological Basis of Therapeutics", which is hereby incorporated herein by reference in its entirety in its entirety, with particular reference to Ch. 1, p. 1). Typically, the dose range of the composition administered to the patient can be from about 0.000001 to 100 mg/kg of the patient's body weight. The dosage may be a single one or a series of two or more given in the course of one or more days, as is needed by the patient. In instances where human dosages for compounds have been established for at least some condition, the present embodiments will use those same dosages, or dosages that are between about 0.1% and 500%, more preferably between about 25% and 250% of the established human dosage.

Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an intravenous, subcutaneous, or intramuscular dose of each active ingredient at an exemplary range of between 0.001 mg and 100 mg, or an exemplary range of between 0.005 mg and 5 mg. In cases of administration of a pharmaceutically acceptable salt, dosages may be calculated as the free base. In some embodiments, the composition is administered 0.1 to 4 times per day or as a single acute dose, for example to ameliorate pain, such as that associated with migraine. Alternatively the compositions as described herein may be administered by continuous intravenous infusion, preferably at a dose of each active ingredient up to 1000 mg per day. As will be understood by those of skill in the art, in certain situations it may be necessary to administer the peptides disclosed herein in amounts that exceed, or even far exceed, the above-stated, exemplary dosage range in order to effectively and aggressively treat particularly aggressive diseases or infections. In some embodiments, the peptides will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each of the compounds but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of the instant composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The instant compositions may, if desired, be presented in a pack or dispenser device which may contain one or more unit dosage forms containing the active ingredient.

Throughout the specification, any recitation of a particular compound should be understood to encompass that compound and any (other) pharmaceutically acceptable salt thereof.

The instant compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose". Amounts effective for this use will depend on the severity of the disease and the weight and general state of the patient.

The compositions described herein can also be microencapsulated by, for example, the method of Tice and Bibi (in: *Treatise on Controlled Drug Delivery*, ed. A. Kydonieus, Marcel Dekker, N.Y. 1992, pp. 315-339), which is hereby incorporated by reference in its entirety.

In prophylactic applications, compositions containing the compounds disclosed herein are administered to a patient susceptible to or otherwise at risk of a particular disease. Such an amount is defined to be a "prophylactically effective dose". In this use, the precise amounts again depend on the patient's state of health and weight, and can be readily determined by one of ordinary skill in the art.

The quantities of the instant antagonist necessary for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, for example, in: Gilman, et al. (eds.), 1990 *Goodman and Gilman's: The Pharmacological Basis of Therapeutics* 8th ed., Pergamon Press; and *Remington's Pharmaceutical Sciences*, 7th Ed., Mack Publishing Co., Easton, Pa. (1985), each of which is hereby incorporated by reference in its entirety. In particular, dosage should be adjusted to accommodate delivery methods such as intramuscular injection, subcutaneous injection, oral delivery or subcutaneous, needle free introduction of the antagonist.

The antagonist peptides and peptidomimetics described herein are effective in treating CGRP receptor mediated conditions when administered at an exemplary dosage range of, for example, from about 0.01 μg to about 50 mg/kg of body weight per day. The specific dose employed is regulated by the particular condition being treated, the route of administration as well as by the judgment of the attending clinician depending upon factors such as the severity of the condition, the age and general condition of the patient, and the like. Such doses can be readily determined by those of skill in the art.

For parenteral administration, the peptides can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (for example, sodium chloride, mannitol) and chemical stability (for example, buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions described herein can be administered as a single dose or in multiple doses; administered either as individual therapeutic agents or in combination with other therapeutic agents; and combined with conventional therapies, which may be administered sequentially or simultaneously.

The compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

The compounds described herein can be formulated into a pharmaceutical composition wherein the compound is the only active agent therein. Alternatively, the pharmaceutical composition can contain additional active agents. Moreover, the peptide compound can be combined with one or more other agents that have modulatory effects on CGRP receptor activity.

Other Utility

The compounds described herein are useful in vitro as unique tools for understanding the biological role of CGRP receptors, including the evaluation of the many factors thought to influence, and be influenced by, the production of ephrin ligands and the receptor binding process. The present compounds are also useful in the development of other compounds that bind to and activate CGRP receptors, because the present compounds provide important information on the relationship between structure and activity to facilitate such development.

The compounds are also useful as competitive binders in assays to screen for new CGRP receptor antagonists. In such assay embodiments, the compounds described herein can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The compounds may also include spacers or linkers in cases where the compounds are to be attached to a solid support.

Nuclear magnetic resonance (NMR) spectroscopy is known for its ability to characterize macromolecular structures, and is a technique for investigating both static and transient features of ligand binding to a target molecule (Pellecchia, et al. 2002 *Nature Rev Drug Disc* 1:211). NMR spectroscopy is a useful tool for determining the binding of ligands to target molecules, and has the advantage of being able to detect and quantify interactions with high sensitivity without requiring prior knowledge of protein function. Furthermore, NMR spectroscopy can provide structural information on both the target and the ligand to aid subsequent optimization of weak-binding hits into high-affinity leads.

Methods of detecting binding of a ligand compound to a target biomolecule by generating first and second nuclear magnetic resonance correlation spectra from target biomolecules which have been uniformly labeled are reported in U.S. Pat. Nos. 5,698,401 and 5,804,390. The first spectrum is generated from data collected on the target substance in the absence of ligands, and the second in the presence of one or more ligands. A comparison of the two spectra permits determination of which compounds in the mixture of putative ligands bind(s) to the target biomolecule.

Moreover, based on their ability to selectively bind to CGRP receptors, the peptides described herein can be used as reagents for selectively detecting CGRP receptors on living cells, fixed cells, in biological fluids, in tissue homogenates, in purified, natural biological materials, etc.

Some embodiments provide modified peptide antagonists that have at least about 60% amino acid sequence identity, alternatively at least about 61% amino acid sequence identity, alternatively at least about 62% amino acid sequence identity, alternatively at least about 63% amino acid sequence identity, alternatively at least about 64% amino acid sequence identity, alternatively at least about 65% amino acid sequence identity, alternatively at least about 66% amino acid sequence identity, alternatively at least about 67% amino acid sequence identity, alternatively at least about 68% amino acid sequence identity, alternatively at least about 69% amino acid sequence identity, alternatively at least about 70% amino acid sequence identity, alternatively at least about 71% amino acid sequence identity, alternatively at least about 72% amino acid sequence identity, alternatively at least about 73% amino acid sequence identity, alternatively at least about 74% amino acid sequence identity, alternatively at least about 75% amino acid sequence identity, alternatively at least about 76% amino acid sequence identity, alternatively at least about 77% amino acid sequence identity, alternatively at least about 78% amino acid sequence identity, alternatively at least about 79% amino acid sequence identity, alternatively at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length polypeptide sequence as disclosed herein (e.g., SEQ ID NOS: 1, 2, 3, 4, 5, 6, 7, 8, 9, 10, 11, 12, 13, 14 or 15) or any other specifically defined fragment of a full-length polypeptide sequence as disclosed herein.

"Percent (%) amino acid sequence identity" with respect to the polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is available as described herein. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 4 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that programs alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of amino acid sequence identity calculations using this method, demonstrated herein is a method to calculate the % amino acid sequence identity of the amino acid sequence designated.

"Comparison peptide" represents the amino acid sequence of a polypeptide against which the polypeptide of interest is being compared, and "X," "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., 1996, *Methods in Enzymology*, 266:460-480). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the polypeptide of interest having a sequence derived from the polypeptide and the comparison amino acid sequence of interest as determined by WU-BLAST-2 by (b) the total number of amino acid residues of the polypeptide of interest. For example, in the statement a polypeptide comprising an the amino acid sequence A which has or having at least 80% amino acid sequence identity to the amino acid sequence B, the amino acid sequence A is the comparison amino acid sequence of interest and the amino acid sequence B is the amino acid sequence of the polypeptide of interest.

Percent amino acid sequence identity may also be determined using the sequence comparison program NCBI-BLAST2 (Altschul et al., 1997, *Nucleic Acids Res.*, 25:3389-3402). The NCBI-BLAST2 sequence comparison program may be downloaded from or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Variations in the sequence of the antagonist peptides described herein, can be made, for example, using any of the techniques and guidelines for conservative and non-conservative mutations set forth, for instance, in U.S. Pat. No. 5,364,934 (Drayna et al., issued Nov. 15, 1994) which is incorporated by reference in its entirety herein. Variations may be a substitution, deletion or insertion of one or more codons encoding the antagonist peptides that results in a change in the amino acid sequence of the antagonist peptides as compared with the reference sequence antagonist peptides. Variations may be according to Table 3, above.

EXAMPLES

The following examples are provided to further illustrate the instant embodiments. They are not meant to limit the scope of the embodiments.

Example 1

Using a calcium flux assay, the dose-dependent inhibitory response of peptide antagonists of the present invention on an amylin receptor, AMY1, a CT (calcitonin) receptor/RAMP1 (receptor-activity modifying protein) complex was determined. The recombinant cell line CHO-K1/AMY1/$G_{\alpha15}$ (GenScript, Piscataway, N.J., Catalog No. M00475) was employed in the assay. Peptide antagonist activities were tested, in duplicate, at five different concentrations, starting with 1 µM and serially diluted five-fold, in DMSO. AC187 (SEQ ID NO: 55), a known amylin receptor antagonist (available for example from Tocris Bioscience, Minneapolis, Minn., Catalog No. 3419) was used as a positive control in the assays, and human α-CGRP, a known amylin receptor agonist (SEQ ID NO:56), (available for example from Tocris Bioscience, Minneapolis, Minn., Catalog No. 3012) was used as a positive control in the assays. The FLIPR® Calcium 4 Assay Kit (Molecular Devices, Sunnyvale, Calif.) was used.

Control Reagents

Human α-CGRP having the amino acid sequence, $NH_2$-ACDTATCVTHRLAGLLSRSGGVVKNN-FVPTNVGSKAF-$NH_2$ (SEQ ID NO:56) and AC187 having the sequence VLGKLSQELHKLQTYPRTNTGSNTY (SEQ ID NO: 55) were employed as negative and positive controls, respectively. Stock solutions were further diluted in HBSS-HEPES buffer to make 5× final control solutions.

TABLE 4

Control Reagents

| Reference compound | M. Wt (g/mol) | Stock solution (Solvent) | Purity (%) | Storage Condition |
|---|---|---|---|---|
| α-CGRP | 3787.32 | 2 mM (DMSO) | 97.1 | −20° C. |
| AC187 | 2849.17 | 50 mM (DMSO) | 99.1 | −20° C. |

Other Reagents

Additional materials used in the assay are provided in Table 5.

TABLE 5

Reagents

| Name | Source | Catalog Number | Accession Number for target protein |
|---|---|---|---|
| CHO-K1/AMY1/$G_{\alpha15}$ | Genscript | M00475 | NM_005855, NM_001742 |
| Probenecid | Sigma | P8761 | N/A |
| FLIPR ® Calcium 4 assay kit | Molecular Devices | R8141 | N/A |

Cell Culture Preparation

CHO-K1/AMY1/$G_{\alpha15}$ cells were seeded in a 384-well black wall, clear bottom plate at a density of 20,000 cells/well in 20 µL of growth medium 20 hours prior to the day of the experiment and maintained at 37° C./5% $CO_2$.

Assay Protocol

Per the assay kit protocol, dye-loading solution (at 2× final concentration) was added into the assay plate, 20 µL per well. Compound solution (at 5× final concentration) was added into the assay plate, 10 uL per well. The assay plate was placed into a 37° C. incubator for 1 hour, then left for 15 min at RT. The agonist plate (at 5×$EC_{80}$ concentration) was placed in Source 2. The total reading time was 120 sec. The agonist was added after 20 seconds reading of the baseline and the fluorescence signal was captured for another 100 seconds (21 s to 120 s).

In screening, cells stimulated with assay buffer were chosen as the background; cells stimulated with agonist (at $EC_{90}$ concentration) were chosen as the negative control.

Data Analysis

Data were recorded by ScreenWorks (version 3.1) as FMD files and stored on the GenScript computer network for offline analysis. Data acquisition and analyses was performed using ScreenWorks (version 3.1) program and exported to Excel. The average value of 20 (1 s to 20 s) seconds reading was calculated as the baseline reading and the relative fluorescent units ($\Delta$RFU) intensity values were calculated with the maximal fluorescent units (21 s to 120 s) subtracting the average value of baseline reading.

The $IC_{50}$ value of AC187 was 8 µM. The inhibitory activity of the tested peptide antagonists was normalized with the negative control (AC187) and reported as % Inhibition, calculated from the following equation:

$$\% \text{ Inhibition} = (\Delta RFU_{Compound} - \Delta RFU_{Background}) / (\Delta RFU_{Negative\ control} - \Delta RFU_{Background}) * 100\%$$

Inhibition was then plotted along the Y-axis, with the test concentrations as indicated on the X-axis. The peptides used are listed in Table 1, above. The results of these experiments are presented in Table 6, with the positive control values listed in Table 7, below. The peptides were tested at indicated concentrations and stimulated with 32 nM ($EC_{80}$) α-CGRP (Mean+/−SD, n=2). The results demonstrate the surprisingly high potency of the selected peptides, for example, many have $IC_{50}$ concentrations in the low nanomolar range compared to the low micromolar range $IC_{50}$ concentration of the positive control, AC187.

TABLE 6

Results.

| SEQ ID. NO | $IC_{50}$ nM | % Inhibition @ Maximal concentration (Mean +/− SD, n = 2) |
|---|---|---|
| 1 | 17 | 94.4 +/− 0.6 |
| 2 | 5 | 96.5 |
| 3 | 4 | 95.9 +/− 2.3 |
| 4 | 12 | 94.6 +/− 0.1 |
| 5 | 75 | 88.5 +/− 0.9 |
| 6 | 33 | 93.9 +/− 0.4 |
| 7 | 8 | 96.0 +/− 1.3 |
| 8 | 16 | 95.4 +/− 0.2 |
| 9 | 9 | 95.6 +/− 0.4 |
| 10 | 9 | 96.8 +/− 0.3 |
| 11 | 9 | 96.5 +/− 0.2 |
| 12 | 9 | 96.1 +/− 0.4 |
| 13 | 4 | 95.8 +/− 0.6 |
| 14 | 1024 | 51.9 +/− 3.3 |
| 15 | 1238 | 23.3 +/− 5.2 |

TABLE 7

Assay Positive Control.

| Peptide | IC$_{50}$ nM |
|---|---|
| AC187 | 8152 |

While the present embodiments have been described in some detail for purposes of clarity and understanding, one skilled in the art will appreciate that various changes in form and detail can be made without departing from the true scope of the embodiments. All figures, tables, and appendices, as well as patents, applications, and publications, referred to above, are hereby incorporated by reference in their entirety.

What is claimed is:

1. A calcitonin gene-related peptide antagonist having the structure of Formula I:

$$X^1\text{-}Y^1\text{-}Z^1 \quad (I),$$

wherein $X^1$ comprises $X^{11}$-$X^{12}$$A^{13}$$A^{14}$$A^{15}$-$X^{16}$-$X^{17}$ (SEQ ID NO: 16) where $X^{17}$ is Cys; and wherein $Y^1$ is -Val-Leu-Gly-Arg-Leu-Ser-Gln-Glu-Leu-His-Arg-Leu-Gln-Thr-Tyr-Pro-Arg-Thr-Asn-(SEQ ID NO: 34); and $Z^1$ is -Val-Gly-Ser-Lys-Ala-Phe-NH$_2$ (SEQ ID NO: 46).

2. The antagonist of claim 1, wherein $X^{11}$ is selected from the group consisting of Ala, Cys, and Gly and wherein $X^{12}$ is selected from the group consisting of Cys, and Ser, provided one of $X^{11}$ and $X^{12}$ is Cys.

3. The antagonist of claim 2, wherein $X^{13}$ is selected from the group consisting of Arg, Asn, Asp, and Val.

4. The antagonist of claim 3, wherein $X^{14}$ is selected from the group consisting of Leu, Phe, and Thr.

5. The antagonist of claim 4, wherein $X^{15}$ is selected from the group consisting of Ala, Gly, and Ser.

6. The antagonist of claim 5, wherein $X^{16}$ is selected from the group consisting of Ala, Ile, Leu, Ser, and Val.

7. The antagonist of claim 1, comprising the amino acid sequence of SEQ ID NO: 1.

8. The antagonist of claim 1, comprising the amino acid sequence of SEQ ID NO: 2.

9. The antagonist of claim 1, comprising the amino acid sequence of SEQ ID NO: 3.

10. The antagonist of claim 1, comprising the amino acid sequence of SEQ ID NO: 4.

11. The antagonist of claim 1, comprising the amino acid sequence of SEQ ID NO: 5.

12. The antagonist of claim 1, comprising the amino acid sequence of SEQ ID NO: 6.

13. The antagonist of claim 1, comprising the amino acid sequence of SEQ ID NO: 7.

14. The antagonist of claim 1, comprising the amino acid sequence of SEQ ID NO: 8.

15. The antagonist of claim 1, comprising the amino acid sequence of SEQ ID NO: 9.

16. The antagonist of claim 1, comprising the amino acid sequence of SEQ ID NO: 10.

17. The antagonist of claim 1, comprising the amino acid sequence of SEQ ID NO: 11.

18. The antagonist of claim 1, comprising the amino acid sequence of SEQ ID NO: 12.

19. The antagonist of claim 1, comprising the amino acid sequence of SEQ ID NO: 57.

20. The antagonist of claim 1, comprising the amino acid sequence of SEQ ID NO: 58.

21. A pharmaceutical composition comprising a pharmaceutically acceptable excipient and a calcitonin gene-related peptide antagonist, said antagonist comprising an amino acid sequence selected from the group consisting of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 or SEQ ID NO: 15.

22. The antagonist of claim 6,
wherein:
$X^1$ is selected from the group consisting of NH$_2$-Ala-Cys-Asp-Thr-Ala-Ala-Cys-(SEQ ID NO: 17), NH$_2$-Ala-Cys-Asp-Thr-Ala-Ser-Cys- (SEQ ID NO: 18), NH$_2$-Ala-Cys-Asp-Thr-Ala-Val-Cys-(SEQ ID NO: 19), NH$_2$-Ala-Cys-Asn-Thr-Ala-Ala-Cys- (SEQ ID NO: 20), NH$_2$-Ala-Cys-Val-Leu-Gly-Ala-Cys- (SEQ ID NO:21), NH$_2$-Ala-Cys-Arg-Phe-Gly-Ala-Cys-(SEQ ID NO: 22), NH$_2$-Ala-Cys-Asp-Leu-Ser-Ala-Cys- (SEQ ID NO: 23), NH$_2$-Ala-Cys-Asn-Leu-Ser-Ala-Cys- (SEQ ID NO: 24), NH$_2$-Cys-Ser-Asn-Thr-Ala-Ala-Cys-(SEQ ID NO: 25), NH$_2$-Ala-Cys-Asp-Thr-Ala-Leu-Cys- (SEQ ID NO: 26), NH$_2$-Ala-Cys-Asp-Thr-Ala-Ile-Cys- (SEQ ID NO: 27), NH$_2$-Ala-Cys-Asp-Leu-Ser-Val-Cys-(SEQ ID NO: 30), NH$_2$-Ala-Cys-Asn-Leu-Ser-Val-Cys (SEQ ID NO: 32) and NH$_2$-Cys-Ser-Asn-Thr-Ala-Val-Cys-(SEQ ID NO: 33);
$Y^1$ is -Val-Leu-Gly-Arg-Leu-Ser-Gln-Glu-Leu-His-Arg-Leu-Gln-Thr-Tyr-Pro-Arg-Thr-Asn-(SEQ ID NO: 34); and
$Z^1$ is -Val-Gly-Ser-Lys-Ala-Phe-NH$_2$ (SEQ ID NO: 46).

23. The antagonist of claim 22 having the structure:
NH$_2$-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 1), NH$_2$-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 2), NH$_2$-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 3), NH$_2$-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 4), NH$_2$-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 5), NH$_2$-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 6), NH$_2$-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 7), NH$_2$-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 8), NH$_2$-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 9), NH$_2$-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 10), NH$_2$-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 11), NH$_2$-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 12), NH$_2$-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 57) or NH$_2$-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$ (SEQ ID NO: 58), or a pharmaceutically acceptable salt thereof.

24. A pharmaceutical composition comprising a pharmaceutically acceptable excipient and a calcitonin gene-related peptide antagonist of claim 1.

25. A method of treating a headache in an individual in need thereof, the method comprising administering to the individual an effective amount of a calcitonin gene-related peptide antagonist of claim 1.

26. The method of claim 25, wherein the headache is a migraine.

27. A method of treating a condition associated with aberrant levels of CGRP comprising the administration of a calcitonin gene-related peptide antagonist of any one of claims 23 and 1, to an individual in need thereof, the method comprising administering to the individual an effective amount of a modified calcitonin gene-related peptide antagonist.

28. The method of claim 27, wherein the condition is a migraine.

\* \* \* \* \*